(12) United States Patent
Lee et al.

(10) Patent No.: US 8,809,297 B2
(45) Date of Patent: Aug. 19, 2014

(54) ANTICANCER COMPOSITION

(75) Inventors: Jae-Seon Lee, Seoul (KR); Bong Cho Kim, Yangju-si (KR); Je-Jung Lee, Goyang-si (KR); Su Min Park, Busan (KR)

(73) Assignee: Korea Institute of Radiological & Medical Sciences, Seoul (KR)

( * ) Notice: Subject to any disclaimer, the term of this patent is extended or adjusted under 35 U.S.C. 154(b) by 0 days.

(21) Appl. No.: 13/700,668

(22) PCT Filed: May 28, 2010

(86) PCT No.: PCT/KR2010/003415
§ 371 (c)(1),
(2), (4) Date: Feb. 28, 2013

(87) PCT Pub. No.: WO2011/149134
PCT Pub. Date: Dec. 1, 2011

(65) Prior Publication Data
US 2013/0149319 A1    Jun. 13, 2013

(51) Int. Cl.
*A61K 48/00*  (2006.01)
*C07H 21/02*  (2006.01)
*C07H 21/04*  (2006.01)
*A61K 39/395* (2006.01)

(52) U.S. Cl.
USPC ......... 514/44; 536/23.1; 536/24.5; 424/130.1

(58) Field of Classification Search
CPC ........... C12Q 1/6886; C12Q 2600/106; C12Q 2600/136; C12N 2310/14
See application file for complete search history.

(56) References Cited

PUBLICATIONS

Scherer et al. (Nat. Biotechnol., 2003, 21(12), pp. 1457-1465).*
Zhang et al. (Current Pharmaceutical Biotechnology 2004, vol. 5, p. 1-7).*
K. Hosono et al.: "YPEL5 protein of the YPEL gene family is involved in the cell cycle progession by interacting with two distinct proteins RanBPM and RanBP10," Genomics, vol. 96, No. 2, pp. 102-111, 2010.
I. Park et al.: "Bmi1, stem cells, and senescence regulation," The Journal of Clinical Investigation, vol. 113, No. 2, pp. 175-179, 2004.
A. Vilborg et al.: "The p53 target Wig-1 regulations p53 mRNA stability through an AU-rich element," PNAS, vol. 106, No. 37, pp. 15756-15761, 2009.
S. Varmeh-Ziaie et al.: "Cloning and chromosomal localization of human WIG-1/PAG608 and demonstration of amplification with increased expression in primary squamous cell carcinoma of the lung," Cancer Letters, vol. 174, No. 2, pp. 179-187, 2001.
M. Sugrue et al.: "Wild-type p53 triggers a rapid senescence program in human tumor cells lacking functional p53," Proc. Natl. Acad. Sci. USA, vol. 94, pp. 9648-9653, 1997.
D. Mason et al.: "Molecular signature of oncogenic ras-induced senescence," Oncogene, vol. 23, pp. 9238-9246, 2004.
M. Hemann et al.: "Oncogenes and senescence: breaking down in the fast lane," Genes and Development, vol. 21:1-5, 6 pages, 2007.
B. Chang et al.: "Molecular determinants of terminal growth arrest induced in tumor cells by a chemotherapeutic agent," PNAS, vol. 99, No. 1, pp. 389-394, 2002.
I. Roninson et al.: "If not apoptosis, then what? Treatment-induced senescence and mitotic catastrophe in tumor cells," Drug Resistance Updates, vol. 4, pp. 303-313, 2001.
J. Campisi: "Suppressing Cancer: The Importance of Being Senescent," Science, vol. 309, pp. 886-887, 2005.
M. Narita et al.: "Senescence comes of age," Nature Medicine, vol. 11, No. 9, pp. 920-922, 2005.
M. Collado et al.: "Senescence in premalignant tumours," Nature, vol. 436, pp. 642, 2005.
W. Xue et al.: "Senescence and tumour clearance is triggered by p53 restoration in murine liver carcinomas," Nature, vol. 445, pp. 656-660, 2007.
A. Rebbaa: "Targeting senescence pathways to reverse drug resistance in cancer," Cancer Letters, vol. 219, pp. 1-13, 2005.
G. Dimri et al.: "A biomarker that identifies senescent human cells in culture and in aging skin in vivo," Proc. Natl. Acad. Sci. USA, vol. 92, pp. 9363-9367, 1995.
M. Bradford: "A Rapid and Sensitive Method for the Quantitation of Microgram Quantities of Protein Utilizing the Principle of Protein-Dye Binding," Analytical Biochemistry, vol. 72, pp. 248-254, 1976.
N. Sinha et al.: "Polymer support oligonucleotide synthesis XVIII: use of beta-cyanoethyl-N,N-dialkylamino-/N-morpholino phosphoramidite of deoxynucleosides for the synthesis of DNA fragments simplifying deprotection and isolation of the final product," Nucleic Acids Research, vol. 12, No. 11, pp. 4539-4557, 1984.

* cited by examiner

*Primary Examiner* — Amy Bowman
(74) *Attorney, Agent, or Firm* — Rothwell, Figg, Ernst & Manbeck, P.C.

(57) ABSTRACT

Disclosed is an anticancer composition, comprising an inhibitor against WIG1 and/or YPEL5 or against a protein encoded by the gene. A composition for screening an anticancer agent comprising a nucleic acid having a sequence complementary to an mRNA of WIG1 and/or YPEL5, or an antibody to a protein encoded by the gene is also provided. Also, a method is provided for screening an anticancer agent, which comprises: (A) quantitatively analyzing expression of WIG1 and/or YPEL5 at an mRNA or protein level in a tumor cell which is not treated with a candidate for an anticancer agent; (B) quantitatively analyzing expression of the gene at an mRNA or protein level in a tumor cell after treatment of the candidate for an anticancer agent; and (C) selecting the candidate if the expression level of the gene is increased in step (B), compared to step (A).

4 Claims, 8 Drawing Sheets

A

B

A

B

A

B

A

B

A

B

A

B

A

B

SEQUENCE LISTING

```
<160> NUMBER OF SEQ ID NOS: 14

<210> SEQ ID NO 1
<211> LENGTH: 9113
<212> TYPE: DNA
<213> ORGANISM: Homo sapiens
<220> FEATURE:
<221> NAME/KEY: mRNA
<222> LOCATION: (1)..(9113)
<223> OTHER INFORMATION: Homo sapiens zinc finger, matrin type 3
      (ZMAT3), transcript variant 2, mRNA. NCBI Accession NM_152240

<400> SEQUENCE: 1
gcagtggcga cgccgagccg gcgccctcag tctcctcctc caccgcctcc cggttccgca      60
gtcacttcct gcagctgttt ccctgtgggt cgggttggac tgacttttga cagtcagcct     120
tcggctgcgg aggggggctcg gcggcggccg gcggagaaag ttgctccgag aagaggctgg    180
gtcgagctgg gccgagccgg gcgcgcaggg cgggcgtcgc gggcgtcccg ggcggacgcg     240
gcgcggagac tgccggcgcg tcccggggt tccggcattt cacgtggacc aggtggatca     300
tctgtgcgtg cagctgcctt ggccctctca gttgcccccg ccccgtggga gtcgggggat     360
tccatccttc gtgatggcat ccataccggg ttgagatttg aagaccttgc ttctcatcac     420
ccactggatt atgccccagg cttccctacc caatgatcct cttgcaacac gccgtgcttc     480
ctccacctaa gcagccctca ccctcgcctc ctatgtcagt ggccaccagg tctacaggaa     540
ccttgcagct tccaccacag aagcctttg ggcaggaggc ttccttgcct cttgcagggg     600
aagaagagtt atcgaaggga ggggagcaag actgtgccct ggaggagcta tgtaagcccc     660
tgtactgcaa actctgcaat gtcaccttga actctgcaca gcaagcccag gctcattatc     720
agggtaaaaa tcatggtaag aaactccgaa attactatgc agcaaatagc tgtcctcctc     780
ctgctagaat gagcaatgtg gtcgagcctg cagctactcc agttgttcca gtccctccgc     840
agatgggctc ctttaagcca ggaggccgag tgatcctggc cacggagaat gattactgta     900
agctctgtga tgcctccttc agttccccag ctgtggctca ggctcactat caagggaaga     960
atcatgccaa gaggctgcgg ctggcggaag ctcagagtaa ctcattctcg gaatcctcag    1020
agctgggtca acggcgggcc aggaaagaag ggaatgagtt taagatgatg cctaacagga    1080
gaaatatgta tacagtacag aataattcag gtccttactt caatccccgc tctcggcaga    1140
gaattccacg tgatctggcc atgtgtgtta ctccaagtgg ccagttttac tgctcaatgt    1200
gtaatgttgg agctggcgaa gagatggaat tccggcagca tttagagagc aagcaacata    1260
agagcaaggt gtctgaacag cggtacagga atgagatgga gaatctggga tatgtatagt    1320
gattatcata ttaagataga gcagcttttc ctgcctgttg tttgccttt gtcaacttgc     1380 cctgctttgt ggtctttttg atatgagtac attcctctgc ttaatgttaa tacatgtaac    1440
ccacagtggt accatgagat gtcaaaacct gggggcccgg gggcggggcg ggggaggtg     1500 ggtgtgaaga acgtgcttct taggtcataa cgcttttgca gggtcaatgg tgttgagccg    1560
ctcatagcat gtgacctacc taccccatca gaaataactt tttatcttgc tcaagttctg    1620
gtcaactagt agcctgacgg cttagaactt tgactattta aaagtttcat tttcttttgc    1680
```

-continued

```
aattttagtt ttatgtactg ttaaagaatt gtactgaatt cttttagat cacagtaaaa    1740
ataggttggc agagatttca gtttcccagg gcttaaccag aaccgccacc tcaatgcatt    1800
gtcagtagaa tacattatta gaaactgtta aggtctttcc cgggacattt ttttctgcca    1860
ttttcttttg caattgtagt tttatgtact gttaaagaat tgtattgaat tcttttaga    1920
tcaaagtaaa aataggtcag cagagatttc agtttcccag ggcttaacca gaaccgccac    1980
ctcaatgcat tgtcagtagg atacattatt agaaactgtt agggtctttc ccaggacatt    2040
ttttttctg tatcatgtct ccccatcatt gaagcgcaaa ttttcttgaa ttcaaatact     2100
cccaatgagc ttgtatactt ccaaacagct aaacttgatt tccagttgtg gatttcacac   2160
atataattgc cgccttcttc cctcctcttt ttttcccccct agttgaatca gcttgtctaa   2220
caagcccatt ttcatgcccc agctgtgctg tgggttttcc aagcctcata tttgaatatt    2280
caatgagttt aagatggata tgatttcaaa aaatagggcc gggcgcggtg gctcacgcct    2340
gtaatcccag cactttggga ggccgaagca ggcggatcac gaggtcagga ggtcgagatc    2400
atcctggcta acacagtgaa accccatctc tactaaaaat acaaaacatt agccgggcgt    2460
ggtggtgggt gcctgtagtc ccagctactc tggaggctga ggcaggagaa tggcgtgaac    2520
ccgggaggcg gagcttgcag tgagccgaga tcgcgccact gcactccagc ctgggtgaca    2580
gagcgagact ccgtctcaaa aaaaaaaaaa aaaaaaaaa aaaatatat atatatatag      2640
atatattttc cagcagtttt taggaaacaa aggtgtgttt gattttccaa tttagagtta    2700
cttcattgat agtaacatgc gcttatatca tgatctaaac cataagttca gattgcttga    2760
tattttgttt tgccagactt ttttgataat ctgattctta cggtttactt acattttcct    2820
ctgtcttgcc agtctggtgg ccatcctgaa aaatatcacc acctgctgtt ttatacacag    2880
aggaatttt taaaaagcaa ataaagtttc actatcttcg tttccagtag aaatatacac    2940
gaactatggt tttattcttt gtaattcggc tttcttgaag atactaacaa gtatatgata    3000
gatcactttg gcatctgata attatatcag tattattatt tttgtttttt tgcgtttaaa    3060
ataagaagtt gtatgaaccc aggaggtgga ggttgcagtc agccaagaat cgtgccactg    3120
cactccagtc tgggcgacag agcaatactc cgtctccaaa aaaaaaaaaa aagaagctat    3180
aatatatatc tagattaact aatggagtgc tctgtgaata ttcattaact acattttatc    3240
tatttactat attttatatg ggtaagacca gtggtcatcc gtatttcttt tgaaagccca    3300
cttgatcagg aagtttatat tttaagcagt atgtttgcac aatggtcagt tcacatttga    3360
ttgcttgtat tactaattag aggtaaaact tctatttttt cttgataatt ctgtaggcaa    3420
aaaaaattgg ggaaggcaaa ttacaatcat tcttcttctg taatactttg ggacaatttt    3480
taaacaactc agacccatgt ttaaaaacga gttttgtgtg attaacccctt gtatagtatc   3540
cagttactgt cttctcttga agtggtggtt cttttgagaag tagaattatt ttgtaacttt    3600
tcttctccca gaaacagaag aatcaaatac tattctgtta ggattctatc tagacctgtg    3660
actcttagta taataacccct tttattatta ttattattat tatttttttca gtaatctata   3720
aagtagagtt gcttagtttt gagcaattta gggcttttct tattggccag taggttattc    3780
attttgctgc taaatataat ttttttggtta attttaacat tatagtgctg gccgcttggt    3840
tctatgatta cctaaaaatc tagtttttt cctccatagg tagatgtgtg tgtatgcata    3900
cccccacaca cacacgtaca tatatgttgt catagagagg tatttcaacc cttattcaa    3960
ataacagtag aagatacgaa catgaattta tattttgtaa aaatgtcatt catccacttt    4020
gttttccatt ggaaatagtt ttataagaag ggttccccctt gctctctcca cttaacaatt    4080
```

```
tcattatata cgtagaaaaa gcagccgact taagggcttg atgttttttc aggccttgtg    4140
gattcaggtt tccagtttcc cagtgccctt aatggatgtt atgaatgcat aagcacattt    4200
tcttttaaag aaagaagtta gatttatagt gttatttctt acttgctata tttctttgca    4260 ctaaaaaga gctatgtgtt tgttttatag gacactttag taccgtattg cctacaataa    4320
ctcagtttgc tccttaaatt ccaaactctg ggaagttgat aaataacttc catgatcact    4380
tgtaaaagtt acatgcacat ctgaaaaaaa atcacaaatc tctatgacag taggttatgt    4440
tttgagcttg ttaccttgca gtattcttct ctgttccata ggtgaaaaca aagggtgaca    4500
gaggttatca ggcaggaaat gcctaaatag atacatctct gcatggtaca atttctcata    4560
ttcatgtatt ccataaacag tgttttttct ctgtttaagc agactgttgt ttcttctgag    4620
tcagtgatat gtgatcttcg ttggtttcat tttgtgaagc tcagtctgtc tctgtaacat    4680
actttaggat ttgcaccttg tgctccccag gaattatgtt agtgtccttt tctatgctgt    4740
cttcaaggat ggacagaggc ctaaaccaca acaacaacaa aaattagaaa aaaaaatact    4800
tagatttcgg taatcatcca taggaactca tagcatcagt ctcttttctc tgtgaataat    4860
atctttgtgt aagttgtcat aaaaaatcaa cgttagaaga tgacaattag aattcttctt    4920
aggtattgag ggtaagaagt tgtaaagaaa gaaaattcgt gtttcaacta aaagattgga    4980
ttgcatatac ctttgaagtg gttttgtaaa aaaagttcag ttactaaact gagtgtgccc    5040
tgtaatcctt ttgagtgcac tgaagatgct ttgaaaatac tttgttggtc ttcacattgt    5100
gcatcatgtc ctgcaacttg taaatatgtg catgttgttt atgtttgtct gcctgtctct    5160
tattgcacta aattctgcaa ggtgaataat ttttttatac catttatttg gaaaaagttc    5220
ctcctccaac tcttcttcac tgacctttta attagttggt aaacttagaa aaccaggtag    5280 gattttttgaa gccctgagtt taaaagaaga atcgtggcta tttgacatca tccttacatt    5340
cccctgactt aaaaagctaa caagaagcac gagatcttcc acctcatttt agaaagcttt    5400
tctacagaac tatatgcttg cttatagcta cctatctaca gtttgaacag ggagaaaggg    5460
agatatgtat gtctggttac atcttccttc actcttgaat tggctgggac agcaagcaac    5520
aacagtttga ggtccagtga cctacgtaaa atgagtgtcg tttgtgtcag gggacacatg    5580
taactgtgca acatggtatt ttctacaggg agggctagga agggtggttt tggaacctaa    5640
cctactttgt gtcttcattg tcagaactaa ggttggaaat gcccttttaaa gaacttggtg    5700 aggcatatgc taggacaata gagctgcttt agaaagaaat tgagacatgt tttgtcagga    5760
cagataaaag tttaatgcag gcttttgaac agatgtttta aaacaaattt gaccttacca    5820 actattttt tcttctagcc aaatcattgt acaggagttt catatatgat aaaaagtgtt    5880
ttgttattgt ttttgctttc ttggcagggg agaaccccta ccattgtgag cagttactgt    5940
cactctggct gaatggacaa atagctgtgt aaatagcttc tcataaaacg cttctactga    6000
tagctgtttg acttttttctt cccgttatga atggaggaa catttgtaaa cttccttttct    6060 gggtagctac caaaaaacgt actggcttat ggtcccatgt gaccttgtct ccgttaagcc    6120
cagaatctga gtgcctttag caagtgttag catttcacag agagaagaga gacagaatta    6180
ttgctattaa tcaccattca taaataggag cttggaataa caaaggtctg tgtgaattct    6240
gttctacgtc ttttttttcc cttttttaaa taaatgtcaa tttgatatca agtaaaacta    6300
ttgtcattat tgatcagaaa ccatacattc tgaaaatgaa tccagtttc ccaagctggc    6360 agaagtcaga gatcattttt caccttgatc tgtgttgcgt ttgtacttag tgaatggcag    6420
```

```
tgtggttgat tggaagagct tgacactgat gtttggaaaa attctttatt ctagtggtca    6480
ttttcaaact tgtcttctgt agagagggga aaaattatgt atttgcagct aaagcgaaga    6540
gactggcaca ataattatta attgtgttag ttcatttcta tattaaatga agcatcttca    6600
caaatcaggt tgaagccat taaaagcaaa attttcccta gtttaattaa tttaaaattc     6660
taaattgcct gactacttag aatcttagaa acgccctgct agactgattt tattatagaa    6720
atgttaacat gttcctcaac attttctcaa gaaaattttc agacatatat caaagttgaa    6780
aaaactttgc agtataacca ctgctagatt ctgccatcaa catttgacta tacttgtatt    6840
gccatgtatc tgttcatatt ctctatccct cttttcatcc atcgatccat cagattttt     6900 ttttaaagaa cattccaaag taaattttag gcaatacact gccctaaatt cttagcatgg    6960
gtgtcattaa ttaaggttta gtattcgttt aaatatctat tttgaaagtg gtgtatgaag    7020
ttgataatct gagccaatta acatactttt ttttttttcc tcctgtggac ttttgtcttc    7080
cagtttctct ttttgtgtgt acttagggtg agggaggaca attcctttca aacacaagtt    7140
tattttagaa ttggtcattt ttaagtgctt gtcataaatt ttaaagtttc aatataattt    7200
ttcttttccc cacttctgat aatgtatttt tgccaaacta tgcagcttct tcaaaaaact    7260
gtaaattact gattggggtt tatgaaatca gcgaataccc catttcaatc tgttgctgct    7320
tttctccctc ttgtcacttc tccttttcact actttcagct gctctaccag aaggtagagg    7380
ggagtaaagg gtcaaacccc tatataatta gctgttttaa acaactctag gagagcagat    7440
taagtagctt agtaagttga aactattaat ttttctaaag aatttgattt gaattccttg    7500
agaattgtaa ttatccacac ttcctccagc tataattagc agaattaaaa atgattgtac    7560
tgtacaatga gttgttgaaa ttgtaagcct tagtaaccat ctttagcttt attgtagtca    7620
tgtttagaaa aaattatttt tacatatgcc tttatttta tgcccacttt ttgtggataa     7680
gattctttag ataaaatcta aagaattta agtgactttc tccaggtcat gaagattcaa     7740
tgggtagaat tgaatcagaa ttgaaatgtt ccagattcat attcttgtgt gtgtttgata    7800
aaattcatgg cttccaaagt aactgaacac ttcctttggg cccttggagg gaaaatccat    7860
atttttacta attcacttt tttttttaga catctggcag ttctttgaac ttaaacatat     7920
tctcatggcc atagttccaa attaagcccg acgcagttgc taaaaatctt gctgcactgt    7980
tgaatactaa taatgcaaca tttattggat gttttgcat tttgatgacc ttcatgattc      8040
atttataagt ctttgtaagt gcttaagtga cccctcact agtgaaaata ataaatgttc      8100
tatatcattt attattattt gtgtattctc tacatgatat atttttttaa ggaagagtaa    8160
ctccacatgt cagaatgagt gatattatcc tagggcaaag cgcaaatagg gcagtttgtt    8220
tctactctgc aaatatggca tgtataggaa caaaactctt ttggagtggc tggtcattgt    8280
tctgccctct tttggtacct gagtaccttt ctggggtttt gtaaatcgtg tgtcatttgt    8340
aagaatttca cgttaactct gcgttacttg gtgttcacct gtggtatcct tgactgacca    8400
taatgattta gtttgggtat gatgtgtctg ctttgaaatg ccttactgga gtatgtcaga    8460
tcctgcttta aagcattcca tatatctgct gggacaataa gttgcttctc cttggaaata    8520
tgctctagat tcagaagcaa aaccgatttt gctttcacca ttaaggttgc attttaatgc    8580
agttattgtt ttaaattaga gaataaaatg taaaaccaag ggaggcttta gaacccttta    8640
ttgaatggca tggcaaactt ttaaaactgc ttttgctatt tcactagaac tatctttgat    8700
aaaggatata gctaaaaaat gtcagcccaa actgtgtgta attaggggttg tttattaaaa    8760 ttttctctaa atgtcataca gaggcttaag atctgtgtat gctgttgggt cggagtgcca    8820
```

```
gtcactgctt tggaagtctg tgttctgggg ctgcagaatg acaaacgtgt catgggatta      8880
aaaccaatca actgtgaatt gtgaaattga aactactctt tcggttttat tttctttagc      8940
atattgagta tagaaatctg aaacttattt aaaatttata ctgcttttgt tgatggctca      9000
ttttggctgt gtatcctcac ttatgtactg atttctgata aaggcttgac attattataa      9060
cacgcatttt gtgttccagt ttaataaaac ggtttctgag tcttgtctga aaa             9113
```

<210> SEQ ID NO 2
<211> LENGTH: 8995
<212> TYPE: DNA
<213> ORGANISM: Homo sapiens
<220> FEATURE:
<221> NAME/KEY: mRNA
<222> LOCATION: (1)..(8995)
<223> OTHER INFORMATION: Homo sapiens zinc finger, matrin type 3
      (ZMAT3), transcript variant 1, mRNA. NCBI ACCESSION No. NM_022470

<400> SEQUENCE: 2

```
gcagtggcga cgccgagccg gcgccctcag tctcctcctc caccgcctcc cggttccgca        60
gtcacttcct gcagctgttt ccctgtgggt cgggttggac tgacttttga cagtcagcct       120
tcggctgcga aggggggctcg gcggcggccg gcggagaaag ttgctccgag aagaggctgg      180
gtcgagctgg gccgagccgg gcgcgcaggg cgggcgtcgc gggcgtcccg ggcggacgcg       240
gcgcggagac tgccggcgcg tcccgggggt tccgatttga agaccttgct tctcatcacc       300
cactggatta tgccccaggc ttccctaccc aatgatcctc ttgcaacacg ccgtgcttcc       360
tccacctaag cagccctcac cctcgcctcc tatgtcagtg gccaccaggt ctacaggaac       420
cttgcagctt ccaccacaga agccttttgg gcaggaggct tccttgcctc ttgcagggga      480
agaagagtta tcgaagggag gggagcaaga ctgtgccctg gaggagctat gtaagcccct       540
gtactgcaaa ctctgcaatg tcaccttgaa ctctgcacag caagcccagg ctcattatca      600
gggtaaaaat catggtaaga aactccgaaa ttactatgca gcaaatagct gtcctcctcc      660
tgctagaatg agcaatgtgg tcgagcctgc agctactcca gttgttccag tccctccgca      720
gatgggctcc tttaagccag gaggccgagt gatcctggcc acgagaatg attactgtaa       780 gctctgtgat gcctccttca gttcccagc tgtggctcag gctcactatc aagggaagaa       840
tcatgccaag aggctgcggc tggcggaagc tcagagtaac tcattctcgg aatcctcaga      900
gctgggtcaa cggcgggcca ggaaagaagg gaatgagttt aagatgatgc ctaacaggag      960
aaatatgtat acagtacaga ataattcagc aggtccttac ttcaatcccc gctctcggca      1020
gagaattcca cgtgatctgg ccatgtgtgt tactccaagt ggccagtttt actgctcaat      1080
gtgtaatgtt ggagctggcg aagagatgga attccggcag catttagaga gcaagcaaca      1140
taagagcaag gtgtctgaac agcggtacag gaatgagatg gagaatctgg atatgtata      1200 gtgattatca tattaagata gagcagcttt tcctgcctgt tgtttgcctt ttgtcaactt      1260
gccctgcttt gtggtctttt tgatatgagt acattcctct gcttaatgtt aatacatgta      1320
acccacagtg gtaccatgag atgtcaaaac ctgggggccc ggggcgggg cgggggagg        1380 tgggtgtgaa gaacgtgctt cttaggtcat aacgcttttg cagggtcaat ggtgttgagc      1440
cgctcatagc atgtgaccta cctaccccat cagaaataac ttttatctt gctcaagttc       1500 tggtcaacta gtagcctgac ggcttagaac tttgactatt taaagtttc attttctttt     1560 gcaattttag tttatgtgac tgttaaagaa ttgtactgaa ttcttttag atcacagtaa       1620 aaataggttg gcagagattt cagtttccca gggcttaacc agaaccgcca cctcaatgca      1680
```

```
ttgtcagtag aatacattat tagaaactgt taaggtcttt cccgggacat tttttctgc    1740
cattttcttt tgcaattgta gttttatgta ctgttaaaga attgtattga attctttta    1800
gatcaaagta aaataggtc agcagagatt tcagtttccc agggcttaac cagaaccgcc    1860
acctcaatgc attgtcagta ggatacatta ttagaaactg ttagggtctt tcccaggaca    1920
ttttttttc tgtatcatgt ctccccatca ttgaagcgca aattttcttg aattcaaata    1980
ctcccaatga gcttgtatac ttccaaacag ctaaacttga tttccagttg tggatttcac    2040
acatataatt gccgccttct tccctcctct ttttccccc ctagttgaat cagcttgtct    2100
aacaagccca ttttcatgcc ccagctgtgc tgtgggtttt ccaagcctca tatttgaata    2160
ttcaatgagt ttaagatgga tatgatttca aaaatagggc cgggcgcgg tggctcacgc    2220
ctgtaatccc agcactttgg gaggccgaag caggcggatc acgaggtcag gagtcgaga    2280
tcatcctggc taacacagtg aaaccccatc tctactaaaa atacaaaaca ttagccgggc    2340
gtggtggtgg gtgcctgtag tcccagctac tctggaggct gaggcaggag aatggcgtga    2400
acccgggagg cggagcttgc agtgagccga tcgcgcca ctgcactcca gcctgggtga    2460
cagagcgaga ctccgtctca aaaaaaaaaa aaaaaaaaa aaaaaatat atatatatat    2520
agatatattt tccagcagtt tttaggaaac aaaggtgtgt ttgattttcc aatttagagt    2580
tacttcattg atagtaacat gcgcttatat catgatctaa accataagtt cagattgctt    2640
gatattttgt tttgccagac tttttgata atctgattct tacggtttac ttacattttc    2700
ctctgtcttg ccagtctggt ggccatcctg aaaaatatca ccacctgctg ttttatacac    2760
agaggaattt tttaaaaagc aaataaagtt tcactatctt cgtttccagt agaaatatac    2820
acgaactatg gttttattct ttgtaattcg gctttcttga agatactaac aagtatatga    2880
tagatcactt tggcatctga taattatatc agtattatta ttttttgtttt tttgcgttta    2940
aaataagaag ttgtatgaac ccaggaggtg gaggttgcag tcagccaaga atcgtgccac    3000
tgcactccag tctgggcgac agagcaatac tccgtctcca aaaaaaaaaa aaaagaagct    3060
ataatatata tctagattaa ctaatggagt gctctgtgaa tattcattaa ctacatttta    3120
tctatttact atattttata tgggtaagac cagtggtcat ccgtatttct tttgaaagcc    3180
cacttgatca ggaagtttat atttttaagca gtatgtttgc acaatggtca gttcacattt    3240
gattgcttgt attactaatt agaggtaaaa cttctatttt ttcttgataa ttctgtaggc    3300
aaaaaaaatt ggggaaggca aattacaatc attcttcttc tgtaatactt tgggacaatt    3360
tttaaacaac tcagacccat gttttaaaaac gagttttgtg tgattaaccc ttgtatagta    3420
tccagttact gtcttctctt gaagtggtgg ttctttgaga agtagaatta ttttgtaact    3480
tttcttctcc cagaaacaga agaatcaaat actattctgt taggattcta tctagacctg    3540
tgactcttag tataataacc cttttattat tattattatt attatttttt cagtaatcta    3600
taaagtagag ttgcttagtt ttgagcaatt tagggctttt cttattggcc agtaggttat    3660
tcattttgct gctaaatata atttttttggt taattttaac attatagtgc tggccgcttg    3720
gttctatgat tacctaaaaa tctagttttt ttcctccata ggtagatgtg tgtgtatgca    3780
tacccccaca cacacacgta catatatgtt gtcatagaga ggtatttcaa cccttatttc    3840
aaataacagt agaagatacg aacatgaatt tatattttgt aaaaatgtca ttcatccact    3900
ttgttttcca ttggaaatag ttttataaga agggttcccc ttgctctctc cacttaacaa    3960
tttcattata tacgtagaaa aagcagccga cttaagggct tgatgttttt tcaggccttg    4020
```

-continued

```
tggattcagg tttccagttt cccagtgccc ttaatggatg ttatgaatgc ataagcacat    4080
tttcttttaa agaaagaagt tagatttata gtgttatttc ttacttgcta tatttctttg    4140
cactaaaaaa gagctatgtg tttgttttat aggacacttt agtaccgtat tgcctacaat    4200
aactcagttt gctccttaaa ttccaaactc tgggaagttg ataaataact tccatgatca    4260
cttgtaaaag ttacatgcac atctgaaaaa aaatcacaaa tctctatgac agtaggttat    4320
gttttgagct tgttaccttg cagtattctt ctctgttcca taggtgaaaa caaagggtga    4380
cagaggttat caggcaggaa atgcctaaat agatacatct ctgcatggta caatttctca    4440
tattcatgta ttccataaac agtgtttttt ctctgtttaa gcagactgtt gtttcttctg    4500
agtcagtgat atgtgatctt cgttggtttc attttgtgaa gctcagtctg tctctgtaac    4560
atactttagg atttgcacct tgtgctcccc aggaattatg ttagtgtcct tttctatgct    4620
gtcttcaagg atggacagag gcctaaacca caacaacaac aaaaattaga aaaaaaata     4680 cttagatttc ggtaatcatc cataggaact catagcatca gtctcttttc tctgtgaata    4740
atatctttgt gtaagttgtc ataaaaaatc aacgttagaa gatgacaatt agaattcttc    4800
ttaggtattg agggtaagaa gttgtaaaga aagaaaattc gtgtttcaac taaaagattg    4860
gattgcatat acctttgaag tggttttgta aaaaagttc agttactaaa ctgagtgtgc     4920
cctgtaatcc ttttgagtgc actgaagatg ctttgaaaat actttgttgg tcttcacatt    4980
gtgcatcatg tcctgcaact tgtaaatatg tgcatgttgt ttatgtttgt ctgcctgtct    5040
cttattgcac taaattctgc aaggtgaata attttttttat accatttatt tggaaaaagt    5100
tcctcctcca actcttcttc actgaccttt taattagttg gtaaacttag aaaaccaggt    5160 aggattttttg aagccctgag tttaaaagaa gaatcgtggc tatttgacat catccttaca   5220
ttcccctgac ttaaaaagct aacaagaagc acgagatctt ccacctcatt ttagaaagct    5280
tttctacaga actatatgct tgcttatagc tacctatcta cagtttgaac agggagaaag    5340
ggagatatgt atgtctggtt acatcttcct tcactcttga attggctggg acagcaagca    5400
acaacagttt gaggtccagt gacctacgta aaatgagtgt cgtttgtgtc aggggacaca    5460
tgtaactgtg caacatggta ttttctacag ggagggctag gaagggtggt tttggaacct    5520
aacctacttt gtgtcttcat tgtcagaact aaggttggaa atgccctttta aagaacttgg   5580 tgaggcatat gctaggacaa tagagctgct ttagaaagaa attgagacat gttttgtcag    5640
gacagataaa agtttaatgc aggcttttga acagatgttt taaaacaaat ttgaccttac    5700
caactatttt tttcttctag ccaaatcatt gtacaggagt ttcatatatg ataaaaagtg    5760
ttttgttatt gttttttgctt tcttggcagg ggagaacccc taccattgtg agcagttact    5820
gtcactctgg ctgaatggac aaatagctgt gtaaatagct tctcataaaa cgcttctact    5880
gatagctgtt tgactttttc ttcccgttat gaatgggagg aacatttgta aacttccttt    5940
ctgggtagct accaaaaaac gtactggctt atggtcccat gtgaccttgt ctccgttaag    6000
cccagaatct gagtgccttt agcaagtgtt agcatttcac agagagaaga gagacagaat    6060
tattgctatt aatcaccatt cataaatagg agcttggaat aacaaaggtc tgtgtgaatt    6120
ctgttctacg tcttttttttt ccctttttta aataaatgtc aatttgatat caagtaaaac    6180
tattgtcatt attgatcaga aaccatacat tctgaaaatg aatccagttt tcccaagctg    6240
gcagaagtca gagatcattt ttcaccttga tctgtgttgc gtttgtactt agtgaatggc    6300
agtgtggttg attggaagag cttgacactg atgtttggaa aaattcttta ttctagtggt    6360
cattttcaaa cttgtcttct gtagagaggg gaaaaattat gtatttgcag ctaaagcgaa    6420
```

```
gagactggca caataattat taattgtgtt agttcatttc tatattaaat gaagcatctt    6480
cacaaatcag gtttgaagcc attaaaagca aaattttccc tagtttaatt aatttaaaat    6540
tctaaattgc ctgactactt agaatcttag aaacgccctg ctagactgat tttattatag    6600
aaatgttaac atgttcctca acattttctc aagaaaattt tcagacatat atcaaagttg    6660
aaaaaacttt gcagtataac cactgctaga ttctgccatc aacatttgac tatacttgta    6720
ttgccatgta tctgttcata ttctctatcc ctcttttcat ccatcgatcc atcagatttt    6780
ttttttaaag aacattccaa agtaaatttt aggcaataca ctgccctaaa ttcttagcat    6840
gggtgtcatt aattaaggtt tagtattcgt ttaaatatct attttgaaag tggtgtatga    6900
agttgataat ctgagccaat taacatactt ttttttttt cctcctgtgg acttttgtct     6960
tccagtttct cttttttgtgt gtacttaggg tgagggagga caattccttt caaacacaag   7020 tttatttag aattggtcat ttttaagtgc ttgtcataaa ttttaaagtt tcaatataat     7080 ttttctttttc cccacttctg ataatgtatt tttgccaaac tatgcagctt cttcaaaaaa   7140
ctgtaaatta ctgattgggg tttatgaaat cagcgaatac ctcatttcaa tctgttgctg    7200
cttttctccc tcttgtcact tctccttca ctactttcag ctgctctacc agaaggtaga    7260
ggggagtaaa gggtcaaacc cctatataat tagctgtttt aaacaactct aggagagcag    7320
attaagtagc ttagtaagtt gaaactatta attttctaa agaatttgat ttgaattcct     7380
tgagaattgt aattatccac acttcctcca gctataatta gcagaattaa aaatgattgt    7440
actgtacaat gagttgttga aattgtaagc cttagtaacc atctttagct ttattgtagt    7500
catgtttaga aaaaattatt tttacatatg cctttatttt tatgcccact ttttgtggat    7560
aagattcttt agataaaatc taagaatttt taagtgactt tctccaggtc atgaagattc    7620
aatgggtaga attgaatcag aattgaaatg ttccagattc atattcttgt gtgtgtttga    7680
taaaattcat ggcttccaaa gtaactgaac acttcctttg ggcccttgga gggaaaatcc    7740 atattttttac taattacact tttttttttta gacatctggc agttctttga acttaaacat   7800
attctcatgg ccatagttcc aaattaagcc cgacgcagtt gctaaaaatc ttgctgcact    7860
gttgaatact aataatgcaa catttattgg atgttttgc attttgatga ccttcatgat     7920
tcatttataa gtctttgtaa gtgcttaagt gaccccctca ctagtgaaaa taataaatgt    7980
tctatatcat ttattattat ttgtgtattc tctacatgat atattttttt aaggaagagt    8040
aactccacat gtcagaatga gtgatattat cctagggcaa agcgcaaata gggcagtttg    8100
tttctactct gcaaatatgg catgtatagg aacaaaactc ttttggagtg ctggtcatt     8160 gttctgccct cttttggtac ctgagtacct ttctggggtt ttgtaaatcg tgtgtcattt    8220
gtaagaattt cacgttaact ctgcgttact tggtgttcac ctgtggtatc cttgactgac    8280
cataatgatt tagtttgggt atgatgtgtc tgctttgaaa tgccttactg gagtatgtca    8340
gatcctgctt taaagcattc catatatctg ctgggacaat aagttgcttc tccttggaaa    8400
tatgctctag attcagaagc aaaaccgatt ttgctttcac cattaaggtt gcattttaat    8460
gcagttattg ttttaaatta gagaataaaa tgtaaaacca agggaggctt tagaacccctt   8520 tattgaatgg catggcaaac ttttaaaact gcttttgcta tttcactaga actatctttg    8580
ataaaggata tagctaaaaa atgtcagccc aaactgtgtg taattagggt tgtttattaa    8640
aattttctct aaatgtcata cagaggctta agatctgtgt atgctgttgg gtcggagtgc    8700
cagtcactgc tttggaagtc tgtgttctgg ggctgcagaa tgacaaacgt gtcatgggat    8760
```

-continued

| | |
|---|---|
| taaaaccaat caactgtgaa ttgtgaaatt gaaactactc tttcggtttt attttcttta | 8820 |
| gcatattgag tatagaaatc tgaaacttat ttaaaattta tactgctttt gttgatggct | 8880 |
| cattttggct gtgtatcctc acttatgtac tgatttctga taaaggcttg acattattat | 8940 |
| aacacgcatt ttgtgttcca gtttaataaa acggtttctg agtcttgtct gaaaa | 8995 |

<210> SEQ ID NO 3
<211> LENGTH: 2281
<212> TYPE: DNA
<213> ORGANISM: Homo sapiens
<220> FEATURE:
<221> NAME/KEY: mRNA
<222> LOCATION: (1)..(2281)
<223> OTHER INFORMATION: Homo sapiens yippee-like 5 (Drosophila)
      (YPEL5), transcript variant 4, mRNA. NCBI ACCESSION No. NM_016061

<400> SEQUENCE: 3

| | |
|---|---|
| ggagagctga ctgcgggggg gcggagccac gccgggtgac tgacgttgag gcccaaccag | 60 |
| ggagaggcgg ggccaaggcc agggcctgac taaacctgga gactcgggtg gccgaggggc | 120 |
| ttcataccag ctgaagagcg acaagccgct ggcagccgcg gatctcaccg ccgctcaggg | 180 |
| tttttagaac ttcagccata aaaatgggca gaattttcct tgatcatatc ggtggtaccc | 240 |
| gtctgttttc ttgtgcaaac tgtgatacga tcctgaccaa ccgctcagaa ctcatctcca | 300 |
| ctcgtttcac aggcgccact ggcagagcat ttcttttttaa caaggtagtt aacctgcagt | 360 |
| acagtgaagt tcaagatcgg gtcatgctca ctggccgcca catggttcga gatgtgagct | 420 |
| gcaaaaactg caatagcaaa ctgggatgga tctatgagtt tgccactgaa acagccagc | 480 |
| gatataagga aggccgcgtg atcctggaac gtgctctagt tcgagagagt gagggctttg | 540 |
| aggagcatgt accatctgat aactcttgaa gatacagaga gaaatccatc ttttcccagg | 600 |
| tctccttcac tgaaaacaaa aatctactta catacactgt caccttagca tcagagtcgg | 660 |
| attaatgaac tgcggaacaa gaggttgtga gaatctaaga tggaaccttt cttttctttct | 720 |
| ttcttttttt ttaaattttg tattttccat ccaacagcag tgtgtagaga gaatattatg | 780 |
| cagatgccgt taattttttta ccctatgttt acatcttgag gcagcagagt ctgtctgcag | 840 |
| ctatgtggtg agctatgtaa ggaaaaaaat ctgggctgtt agagtgaaaa agtgtgttttt | 900 |
| atgtcaattg tgaaaggaaa atgttaggag tatggttttt aaacttgggc ttcattttaa | 960 |
| acttttttttt ttaaacccag ttatttcact tgatttgcta gcttcagaga agagatccga | 1020 |
| atctgtgccc agcgctaaag gctcagtgtt agcatggctt gtgctggccg gtgtgccata | 1080 |
| ttcttgttgg agatgaaccg tagcaccaga gcccattctt ccttgtcagt cttggcccaa | 1140 |
| agatgtcacc attcctagtt atttgtcacc acataattgg tgttgattgg aaacttttc | 1200 |
| tgagatggga cagaactgct gggttgtctt tttccatgta acttaagcat agtaatataa | 1260 |
| ataaagtaat agttggatgc ttttggtcct gtgttgcttt taaaaacacc ttataaaaga | 1320 |
| ggagagtatt tgataagcaa ttttcatagt agtaaagttt ttttttcatct cttaaactaa | 1380 |
| attgaccatg catataatat tctttgttta aatgaaagca tactgttgaa acccgcagtg | 1440 |
| ttgcatttag aaaacagttg aacagaatgt caatgtgcat tcatgcaaaa aaacatttaa | 1500 |
| tctgcatctg ttttagaaaa gggggaaatg aagcaacttg tctaaaaata ctgctttaca | 1560 |
| aagcatttca gcctttcccc ctcagttttg cattgatttt ttgacaagtc tgtagagcct | 1620 |
| aatagttttcc atcaaaggcc tagatctctt atttagcatt ttttttcagct cttctctcag | 1680 |
| aagttcagct gttgaaacga aaactgtact ttgtaccctc acatacaaag ggatcaaatt | 1740 |

-continued

| | |
|---|---|
| tgacctggtg ttatttagc cccaaattta tgacattaca caatattaaa atgtaaatgt | 1800 |
| ttctttaccc aaactacttc tagatattct agtatttgct tctggtggaa ttaaatgacg | 1860 |
| gtaaaattgg ctaattattt gaatgaatga atggatggat gttttgcatg ctcaatttct | 1920 |
| aggtcctttg tctagaaagg aaatttgcct cagttgaatt agtgaaatat ttctgtcgtt | 1980 |
| gatattaaaa gtgacttctg agtacagtta agttcctcct atttgccact gggctgttgg | 2040 |
| ttagaagcat aggtaactga ttaagtaggt atgatactgc atttgaaata agtggacaca | 2100 |
| aactatcctt tctccaccat ggactcaatc tgagaacaac agcattcatt tccattcatt | 2160 |
| tccatactgg cttttgatta tatgcagatt cctagtagca tgccttacct acagcactat | 2220 |
| gtgcatttgc tgtcacaata agtatattt tgtcttgcaa aaaaaaaaa aaaaaaaaa | 2280 |
| a | 2281 |

<210> SEQ ID NO 4
<211> LENGTH: 2639
<212> TYPE: DNA
<213> ORGANISM: Homo sapiens
<220> FEATURE:
<221> NAME/KEY: mRNA
<222> LOCATION: (1)..(2639)
<223> OTHER INFORMATION: Homo sapiens yippee-like 5 (Drosophila)
    (YPEL5), transcript variant 1, mRNA. NCBI ACCESSION No.
    NM_001127401

<400> SEQUENCE: 4

| | |
|---|---|
| ggagagctga ctgcgggggg gcggagccac gccgggtgac tgacgttgag gcccaaccag | 60 |
| ggagaggcgg ggccaaggcc agggcctgac taaacctgga gactcgggtg gccgaggggc | 120 |
| ttcataccag ctgaagagcg acaagccgct ggcagccgcg gatctcaccg ccgctcagga | 180 |
| gatctgttgg taatctgagg attttttattc tacgtcgtct tgacagatgg aaaacctgaa | 240 |
| gtaacttcgg gctaaccttg tgttttggaa aaattagtag acttggtggt gaagaaactg | 300 |
| ggaggagtag gatattagct aactttgcat agccacatat agagcgtcgc agctgcattc | 360 |
| caccaaagag gaaccaaaag gcctgtggtg ttcccagggt acatattcat gccagaagtg | 420 |
| aagtgctttg gtgaattcgt ttcctgaaag tttatcgcat acttgtactg ggttagcctt | 480 |
| atgccagcct ggaccatctt ggaggcagtg taggatcatg gaagaacttt gaattaggtt | 540 |
| tttagaactt cagccataaa aatgggcaga attttccttg atcatatcgg tggtacccgt | 600 |
| ctgttttctt gtgcaaactg tgatacgatc ctgaccaacc gctcagaact catctccact | 660 |
| cgtttcacag gcgccactgg cagagcattt cttttaaca aggtagttaa cctgcagtac | 720 |
| agtgaagttc aagatcgggt catgctcact ggccgccaca tggttcgaga gtgagctgc | 780 |
| aaaaactgca atagcaaact gggatggatc tatgagtttg ccactgaaga cagccagcga | 840 |
| tataaggaag gccgcgtgat cctggaacgt gctctagttc gagagagtga gggctttgag | 900 |
| gagcatgtac catctgataa ctcttgaaga tacagagaga atccatcttt tcccaggtc | 960 |
| tccttcactg aaaacaaaaa tctacttaca tacactgtca ccttagcatc agagtcggat | 1020 |
| taatgaactg cggaacaaga ggttgtgaga atctaagatg gaacctttct ttctttcttt | 1080 |
| cttttttttt aaattttgta ttttccatcc aacagcagtg tgtagagaga atattatgca | 1140 |
| gatgccgtta atttttacc ctatgtttac atcttgaggc agcagagtct gtctgcagct | 1200 |
| atgtggtgag ctatgtaagg aaaaaaatct gggctgttag agtgaaaaag tgtgttttat | 1260 |
| gtcaattgtg aaaggaaaat gttaggagta tggttttttaa acttgggctt cattttaaac | 1320 |
| ttttttttt aaacccagtt atttcacttg atttgctagc ttcagagaag agatccgaat | 1380 |

```
ctgtgcccag cgctaaaggc tcagtgttag catggcttgt gctggccggt gtgccatatt    1440
cttgttggag atgaaccgta gcaccagagc ccattcttcc ttgtcagtct tggcccaaag    1500
atgtcaccat tcctagttat ttgtcaccac ataattggtg ttgattggaa acttttctg    1560 agatgggaca gaactgctgg gttgtctttt tccatgtaac ttaagcatag taatataaat    1620
aaagtaatag ttggatgctt ttggtcctgt gttgctttta aaaacacctt ataaagagg    1680 agagtatttg ataagcaatt ttcatagtag taaagttttt tttcatctct taaactaaat    1740
tgaccatgca tataatattc tttgtttaaa tgaaagcata ctgttgaaac ccgcagtgtt    1800
gcatttagaa aacagttgaa cagaatgtca atgtgcattc atgcaaaaaa acatttaatc    1860
tgcatctgtt ttagaaaagg gggaaatgaa gcaacttgtc taaaaatact gctttacaaa    1920
gcatttcagc ctttccccct cagttttgca ttgattttt gacaagtctg tagagcctaa    1980
tagtttccat caaaggccta gatctcttat ttagcatttt tttcagctct tctctcagaa    2040
gttcagctgt tgaaacgaaa actgtacttt gtaccctcac atacaaaggg atcaaatttg    2100
acctggtgtt attttagccc caaatttatg acattacaca atattaaaat gtaaatgttt    2160
ctttacccaa actacttcta gatattctag tatttgcttc tggtggaatt aaatgacggt    2220
aaaattggct aattatttga atgaatgaat ggatggatgt tttgcatgct caatttctag    2280
gtcctttgtc tagaaggaa atttgcctca gttgaattag tgaaatattt ctgtcgttga    2340
tattaaaagt gacttctgag tacagttaag ttcctcctat ttgccactgg gctgttggtt    2400
agaagcatag gtaactgatt aagtaggtat gatactgcat ttgaaataag tggacacaaa    2460 ctatccttc tccaccatgg actcaatctg agaacaacag cattcatttc cattcatttc    2520
catactggct tttgattata tgcagattcc tagtagcatg ccttacctac agcactatgt    2580
gcatttgctg tcacaataaa gtatattttg tcttgcaaaa aaaaaaaaa aaaaaaaa     2639
```

<210> SEQ ID NO 5
<211> LENGTH: 2578
<212> TYPE: DNA
<213> ORGANISM: Homo sapiens
<220> FEATURE:
<221> NAME/KEY: mRNA
<222> LOCATION: (1)..(2578)
<223> OTHER INFORMATION: Homo sapiens yippee-like 5 (Drosophila)
      (YPEL5), transcript variant 2, mRNA. NCBI ACCESSION No.
      NM_001127400

<400> SEQUENCE: 5

```
ggagagctga ctgcggggg gcggagccac gccgggtgac tgacgttgag gcccaaccag      60
ggagaggcgg ggccaaggcc agggcctgac taaacctgga gactcgggtg gccgaggggc     120
ttcataccag ctgaagagcg acaagccgct ggcagccgcg gatctcaccg ccgctcagga     180
gatctgttgg taatctgagg attttttatt ctacgtcgtct tgacagatgg aaaacctgaa    240
gtaacttcgg gctaaccttg tgttttttgga aaattagtag acttggtggt gaagaaactg    300
ggaggagtag gatattagct aactttgcat agccacatat agagcgtcgc agctgcattc    360
caccaaagag gaaccaaaag gcctgtggtg ttcccagggt acatattcat gccagaagtg    420
aagtgctttg gtgaattcgt ttcctgaaag tttatcgcat acttgtactg ggttaggttt    480
ttagaacttc agccataaaa atgggcagaa ttttccttga tcatatcggt ggtacccgtc    540
tgttttcttg tgcaaactgt gatacgatcc tgaccaaccg ctcagaactc atctccactc    600
gtttcacagg cgccactggc agagcatttc tttttaacaa ggtagttaac ctgcagtaca    660
```

| | | |
|---|---|---|
| gtgaagttca agatcgggtc atgctcactg gccgccacat ggttcgagat gtgagctgca | 720 | |
| aaaactgcaa tagcaaactg ggatggatct atgagtttgc cactgaagac agccagcgat | 780 | |
| ataaggaagg ccgcgtgatc ctggaacgtg ctctagttcg agagagtgag ggctttgagg | 840 | |
| agcatgtacc atctgataac tcttgaagat acagagagaa atccatcttt tcccaggtct | 900 | |
| ccttcactga aaacaaaaat ctacttacat acactgtcac cttagcatca gagtcggatt | 960 | |
| aatgaactgc ggaacaagag gttgtgagaa tctaagatgg aacctttctt tctttctttc | 1020 | |
| ttttttttta aattttgtat tttccatcca acagcagtgt gtagagagaa tattatgcag | 1080 | |
| atgccgttaa ttttttaccc tatgtttaca tcttgaggca gcagagtctg tctgcagcta | 1140 | |
| tgtggtgagc tatgtaagga aaaaaatctg ggctgttaga gtgaaaaagt gtgttttatg | 1200 | |
| tcaattgtga aaggaaaatg ttaggagtat ggttttaaaa cttgggcttc attttaaact | 1260 | |
| tttttttta aacccagtta tttcacttga tttgctagct tcagagaaga gatccgaatc | 1320 | |
| tgtgcccagc gctaaaggct cagtgttagc atggcttgtg ctggccggtg tgccatattc | 1380 | |
| ttgttggaga tgaaccgtag caccagagcc cattcttcct tgtcagtctt ggcccaaaga | 1440 | |
| tgtcaccatt cctagttatt tgtcaccaca taattggtgt tgattggaaa cttttttctga | 1500 | |
| gatgggacag aactgctggg ttgtctttt ccatgtaact taagcatagt aatataaata | 1560 | |
| aagtaatagt tggatgcttt tggtcctgtg ttgcttttaa aaacaccttta taaaagagga | 1620 | |
| gagtatttga taagcaattt tcatagtagt aaagtttttt ttcatctctt aaactaaatt | 1680 | |
| gaccatgcat ataatattct ttgtttaaat gaaagcatac tgttgaaacc cgcagtgttg | 1740 | |
| catttagaaa acagttgaac agaatgtcaa tgtgcattca tgcaaaaaaa catttaatct | 1800 | |
| gcatctgttt tagaaagggg ggaaatgaag caacttgtct aaaaatactg ctttacaaag | 1860 | |
| catttcagcc tttccccctc agtttttgcat tgattttttg acaagtctgt agagcctaat | 1920 | |
| agtttccatc aaaggcctag atctcttatt tagcatttt ttcagctctt ctctcagaag | 1980 | |
| ttcagctgtt gaaacgaaaa ctgtactttg taccctcaca tacaaaggga tcaaatttga | 2040 | |
| cctggtgtta ttttagcccc aaatttatga cattacacaa tattaaaatg taaatgtttc | 2100 | |
| tttacccaaa ctacttctag atattctagt atttgcttct ggtggaatta aatgacggta | 2160 | |
| aaattggcta attatttgaa tgaatgaatg gatggatgtt ttgcatgctc aatttctagg | 2220 | |
| tcctttgtct agaaaggaaa tttgcctcag ttgaattagt gaaatatttc tgtcgttgat | 2280 | |
| attaaaagtg acttctgagt acagttaagt tcctcctatt tgccactggg ctgttggtta | 2340 | |
| gaagcatagg taactgatta agtaggtatg atactgcatt tgaaataagt ggacacaaac | 2400 | |
| tatcctttct ccaccatgga ctcaatctga gaacaacagc attcatttcc attcatttcc | 2460 | |
| atactggctt ttgattatat gcagattcct agtagcatgc cttacctaca gcactatgtg | 2520 | |
| catttgctgt cacaataaag tatatttgt cttgcaaaaa aaaaaaaaa aaaaaaa | 2578 | |

```
<210> SEQ ID NO 6
<211> LENGTH: 2342
<212> TYPE: DNA
<213> ORGANISM: Homo sapiens
<220> FEATURE:
<221> NAME/KEY: mRNA
<222> LOCATION: (1)..(2342)
<223> OTHER INFORMATION: Homo sapiens yippee-like 5 (Drosophila)
      (YPEL5), transcript variant 3, mRNA.NCBI ACCESSION No.
      NM_001127399

<400> SEQUENCE: 6
```

| | |
|---|---|
| ggagagctga ctgcgggggg gcggagccac gccgggtgac tgacgttgag gcccaaccag | 60 |

```
ggagaggcgg ggccaaggcc agggcctgac taaacctgga gactcgggtg gccgaggggc    120
ttcataccag ctgaagagcg acaagccgct ggcagccgcg gatctcaccg ccgctcagga    180
gatctgttgg taatctgagg attttttattc tacgtcgtct tgacagatgg aaaacctgaa    240
gtttttagaa cttcagccat aaaaatgggc agaattttcc ttgatcatat cggtggtacc    300
cgtctgtttt cttgtgcaaa ctgtgatacg atcctgacca accgctcaga actcatctcc    360
actcgtttca caggcgccac tggcagagca tttcttttta acaaggtagt taacctgcag    420
tacagtgaag ttcaagatcg ggtcatgctc actggccgcc acatggttcg agatgtgagc    480
tgcaaaaact gcaatagcaa actgggatgg atctatgagt ttgccactga agacagccag    540
cgatataagg aaggccgcgt gatcctggaa cgtgctctag ttcgagagag tgagggcttt    600
gaggagcatg taccatctga taactcttga agatacagag agaaatccat cttttcccag    660
gtctccttca ctgaaaacaa aaatctactt acatacactg tcaccttagc atcagagtcg    720
gattaatgaa ctgcggaaca agaggttgtg agaatctaag atggaacctt tctttctttc    780
tttctttttt tttaaatttt gtattttcca tccaacagca gtgtgtagag agaatattat    840
gcagatgccg ttaatttttt accctatgtt tacatcttga ggcagcagag tctgtctgca    900
gctatgtggt gagctatgta aggaaaaaaa tctgggctgt tagagtgaaa aagtgtgttt    960
tatgtcaatt gtgaaaggaa aatgttagga gtatggtttt taaacttggg cttcatttta   1020 aactttttt tttaaaccca gttatttcac ttgatttgct agcttcagag aagagatccg    1080
aatctgtgcc cagcgctaaa ggctcagtgt tagcatggct tgtgctggcc ggtgtgccat   1140
attcttgttg gagatgaacc gtagcaccag agcccattct tccttgtcag tcttggccca   1200
aagatgtcac cattcctagt tatttgtcac cacataattg gtgttgattg gaaacttttt   1260
ctgagatggg acagaactgc tgggttgtct ttttccatgt aacttaagca tagtaatata   1320
aataaagtaa tagttggatg cttttggtcc tgtgttgctt ttaaaaacac cttataaaag   1380
aggagagtat ttgataagca attttcatag tagtaaagtt ttttttcatc tcttaaacta   1440
aattgaccat gcatataata ttctttgttt aaatgaaagc atactgttga aacccgcagt   1500
gttgcattta gaaaacagtt gaacagaatg tcaatgtgca ttcatgcaaa aaacattta    1560 atctgcatct gttttagaaa agggggaaat gaagcaactt gtctaaaaat actgctttac   1620
aaagcatttc agccttttccc cctcagtttt gcattgattt tttgacaagt ctgtagagcc   1680
taatagtttc catcaaaggc ctagatctct tatttagcat ttttttcagc tcttctctca   1740
gaagttcagc tgttgaaacg aaaactgtac tttgtacccct cacatacaaa gggatcaaat   1800
ttgacctggt gttatttag ccccaaattt atgacattac acaatattaa aatgtaaatg    1860 tttcttacc caaactactt ctagatattc tagtatttgc ttctggtgga attaaatgac    1920
ggtaaaattg gctaattatt tgaatgaatg aatggatgga tgttttgcat gctcaatttc    1980
taggtccttt gtctagaaag gaaatttgcc tcagttgaat tagtgaaata ttctgtcgt    2040 tgatattaaa agtgacttct gagtacagtt aagttcctcc tatttgccac tgggctgttg   2100
gttagaagca taggtaactg attaagtagg tatgatactg catttgaaat aagtggacac   2160
aaactatcct ttctccacca tggactcaat ctgagaacaa cagcattcat ttccattcat   2220
ttccatactg gcttttgatt atatgcagat tcctagtagc atgccttacc tacagcacta   2280
tgtgcatttg ctgtcacaat aaagtatatt ttgtcttgca aaaaaaaaaa aaaaaaaaa    2340 aa                                                                  2342
```

```
<210> SEQ ID NO 7
<211> LENGTH: 19
<212> TYPE: RNA
<213> ORGANISM: Artificial Sequence
<220> FEATURE:
<223> OTHER INFORMATION: sense of siRNA for WIG1

<400> SEQUENCE: 7
ugagcuugua uacuuccaa                                              19

<210> SEQ ID NO 8
<211> LENGTH: 19
<212> TYPE: RNA
<213> ORGANISM: Artificial Sequence
<220> FEATURE:
<223> OTHER INFORMATION: antisense of siRNA for WIG1

<400> SEQUENCE: 8
uuggaaguau auaagcuca                                              19

<210> SEQ ID NO 9
<211> LENGTH: 19
<212> TYPE: RNA
<213> ORGANISM: Artificial Sequence
<220> FEATURE:
<223> OTHER INFORMATION: sense of siRNA for YPEL5

<400> SEQUENCE: 9
gcuggguugu cuuuuucca                                              19

<210> SEQ ID NO 10
<211> LENGTH: 19
<212> TYPE: RNA
<213> ORGANISM: Artificial Sequence
<220> FEATURE:
<223> OTHER INFORMATION: antisense of siRNA for YPEL5

<400> SEQUENCE: 10
uggaaaaaga caacccagc                                              19

<210> SEQ ID NO 11
<211> LENGTH: 50
<212> TYPE: DNA
<213> ORGANISM: Artificial Sequence
<220> FEATURE:
<223> OTHER INFORMATION: DNA probe for WIG1

<400> SEQUENCE: 11
ggtcagcaga gatttcagtt tcccagggct taaccagaac cgccacctca             50

<210> SEQ ID NO 12
<211> LENGTH: 50
<212> TYPE: DNA
<213> ORGANISM: Artificial Sequence
<220> FEATURE:
<223> OTHER INFORMATION: DNA probe for YPEL5

<400> SEQUENCE: 12
gtgacttctg agtacagtta agttcctcct atttgccact gggctgttgg             50

<210> SEQ ID NO 13
<211> LENGTH: 19
<212> TYPE: RNA
<213> ORGANISM: Artificial Sequence
<220> FEATURE:
<223> OTHER INFORMATION: sense of non-specific siRNA
```

```
<400> SEQUENCE: 13
ccuacgccac caauuucgu                                                    19

<210> SEQ ID NO 14
<211> LENGTH: 19
<212> TYPE: RNA
<213> ORGANISM: Artificial Sequence
<220> FEATURE:
<223> OTHER INFORMATION: antisense of non-specific siRNA

<400> SEQUENCE: 14
acgaaauugg uggcguagg                                                    19
```

ANTICANCER COMPOSITION

CROSS REFERENCE TO RELATED APPLICATIONS

This application is a 35 U.S.C. §371 National Phase Entry Application from PCT/KR2010/003415, filed May 28, 2010, and designating the United States, which is incorporated herein in its entirety.

TECHNICAL FIELD

The present invention relates to an anticancer composition, a composition for screening anticancer agents, and a method of screening anticancer agents. More particularly, the present invention relates to the application of the induction of premature senescence in tumor cells to an anticancer composition, a composition for screening anticancer agents, and a method of screening anticancer agents.

BACKGROUND ART

Premature senescence, also known as stress-induced premature senescence, in tumor cells means senescence caused in tumor cells by various stimuli. In contrast to normal cells that undergo senescence after a particular number of cell doublings, cells under tumorigenesis divide uncontrollably without replicative senescence. It has long been known that tumor cells may not undergo cellular senescence. In recent years, however, various stimuli have been known to rapidly induce senescence in tumor cells, which is called stress-induced premature senescence (Sugrue et al., Proc. Natl. Acad. Sci. USA, 94:9648-9653, 1997; Mason et al., Oncogene, 23; 9238-9246, 2004). Representatives among the stress sources capable of inducing senescence in tumor cells are genotoxic chemicals (e.g., etoposide, cyclophophamide, etc.), radiation, and UV light (Hemann and Narita, Genes & Dev., 21:1-5, 2007; Chang et al., Proc. Natl. Acad. Sci. USA, 99: 389-394, 2002).

Suppression of tumor cell growth (proliferation) by inducing senescence in tumor cells through stress-induced premature senescence was suggested as a mechanism for cancer therapy (Roninson et al., Drug Resist Updates, 4:303-313, 2001; Campisi, Science, 309:886-887, 2005), and studies on the mechanism of cellular senescence contributed to an improvement in the efficiency of cancer therapy (Narita and Lowe, Nature Medicine, 11:920-922, 2005). Also, a histological analysis of cancer patients who had the cease of the malignant progression of tumor reported that senescence was effectively induced in tumor cells (Collado et al., Nature, 436:642, 2005). In addition, the tumor suppressor p53 was reported to be implicated in the removal of tumor tissues through cellular senescence, as proven in an animal test (Xue et al., Nature, 445:656-660, 2007). This indicates that cellular senescence can be effectively applied to cancer therapy. In practice, the activation of the senescence mechanism in tumor cells makes it possible to treat cancer with lower doses of anticancer agents or radiation than does the activation of cell death mechanisms, thus improving the side effects associated with conventional cancer therapy and overcoming the resistance of cancer cells to cancer therapy which acquire the resistance to the cell death (Rebbaa, Cancer Lett, 219:1-13, 2005).

There is therefore a need for an anticancer agent based on premature senescence and a method for screening the anticancer agent.

Nowhere have WIG1 (wild-type p53 induced gene-1; ZMAT3, zinc finger matrin type 3), a gene with NCBI Access No. NM_152240 or NM_022470, and YPEL5 [yippee-like 5 (Drosophila)], a gene with NCBI Access No. NM_016061, NM_001127401, NM_001127400, or NM_001127399, been known to be associated with premature senescence in tumor cells in the prior art.

DISCLOSURE

Technical Problem

It is an object of the present invention to provide an anticancer composition.

It is another object of the present invention to provide a composition for screening an anticancer agent.

It is a further object of the present invention to provide a method for screening an anticancer agent.

Technical Solution

In accordance with an aspect thereof, the present invention addresses an anticancer composition comprising an inhibitor against a gene selected from the group consisting of WIG1 (wild-type p53 induced gene-1; also known as ZMAT3, zinc finger matrin type 3), YPEL5 (yippee-like 5) and a combination thereof, or against a protein encoded by the gene.

As used herein, the term "anticancer" is intended to encompass the effect by premature senescence in tumor cells.

In one embodiment of the present invention, the gene may be an mRNA (messenger ribonucleic acid) and the inhibitor may be siRNA (small interfering RNA) inhibitory of the mRNA. In a preferred embodiment, the siRNA may have the sense sequence of SEQ ID NO: 7 (for WIG1) or SEQ ID NO: 9 (for YPEL5), and may preferably be a double stranded siRNA composed of the sense sequence and an antisense sequence complementary to the sense sequence. In another preferred embodiment, the double-stranded siRNA may be composed of the sense sequence of SEQ ID NO: 7 or 9 and the antisense sequence of SEQ ID NO: 8 or 10, respectively. In a further preferred embodiment, the siRNA has two tandem thymine residues (dTdT) at the 3' terminus of the sense and/or the antisense sequence.

In another embodiment of the present invention, the inhibitor against a protein may be an antibody specifically binding to the protein. The antibody useful in the present invention may be a monoclonal antibody, a polyclonal antibody, and/or a recombinant antibody, and may be a commercially available product or may be directly prepared using a well-known method (Benny K. C. Lo ed., Antibody Engineering: Methods and Protocols, Methods in Molecular Biology, Vol. 248, Humana Press (2004)).

Preferably, the composition of the present invention may be a pharmaceutical composition. In the composition of the present invention, the inhibitor induces senescence in tumor cells, thus exhibiting anticancer activity.

In accordance with another aspect thereof, the present invention is concerned with a composition for screening an anticancer agent, comprising a nucleic acid having a sequence complementary to mRNA of a gene selected from the group WIG1, YPEL5 and a combination thereof, or an antibody to a protein encoded by the gene.

In one embodiment of the present invention, the nucleic acid may be a DNA (deoxyribonucleic acid) complementary to the mRNA. The DNA may be a probe useful in a commercially available DNA chip or may be directly synthesized using a well-known method (Piet Herdewijn ed., Oligonucleotide Synthesis: Methods and Applications, Methods in Molecular Biology, Vol. 288, Humana Press (2005)). Preferably, the DNA complementary to the mRNA may have the nucleotide sequence of SEQ ID NO: 11 (for WIG1) or SEQ ID NO: 12 (for YPEL5).

The antibody useful in the present invention may be a monoclonal antibody, a polyclonal antibody, and/or a recombinant antibody, and may be a commercially available product or may be directly prepared using a well-known method (Benny K. C. Lo ed., Antibody Engineering: Methods and Protocols, Methods in Molecular Biology, Vol. 248, Humana Press (2004)).

The anticancer agent induces premature senescence in tumor cells so as to exert anticancer effects, and may be preferably selected from among a gene inhibitor, an antibody and a combination thereof. In a preferred embodiment, the gene inhibitor may be siRNA.

In accordance with a further aspect thereof, the present invention is concerned with a method for screening an anticancer agent, comprising: (A) quantitatively analyzing the expression of a gene selected from the group consisting of WIG1, YPEL5 and a combination thereof at an mRNA or protein level in a tumor cell which is not treated with a candidate for the anticancer agent; (B) quantitatively analyzing the expression of the gene at an mRNA or protein level in a tumor cell treated with the candidate; and (C) selecting the candidate as an anticancer agent if the expression level of the gene is increased after treatment of the candidate for the anticancer agent. Herein, the tumor cell which is not treated with a candidate may be a tumor cell before treatment with the candidate.

As used herein, the term "candidate for an anticancer agent" is intended to encompass an agent predictable to exert an anticancer effect, and may be selected from the group consisting of, but not limited to, radiation, a gene inhibitor, an antibody and a combination thereof. The gene inhibitor may be preferably siRNA.

In the screening method of the present invention, quantitative analysis at an mRNA level may be performed with a nucleic acid complementary to the mRNA. Preferably, the nucleic acid may be a DNA complementary to the mRNA. The DNA may be a probe useful in a commercially available DNA chip, or may be directly synthesized using a well-known method. Preferably, the DNA complementary to the mRNA may have the nucleotide sequence of SEQ ID NO: 11 (for WIG1) or SEQ ID NO: 12 (for YPEL5).

In the screening method of the present invention, the mRNA level may be determined using reverse transcription polymerase chain reaction (RT-PCR), competitive RT-PCR, real-time PCR, Northern blotting or a DNA chip.

In the screening method of the present invention, quantitative analysis at a protein level may be performed with an antibody which binds specifically to the protein. The antibody may be a monoclonal antibody, polyclonal antibody or a recombinant antibody, and may be a commercially available product or may be directly prepared using a well-known method (Benny K. C. Lo ed., Antibody Engineering: Methods and Protocols, Methods in Molecular Biology, Vol. 248, Humana Press (2004)).

In the screening method of the present invention, the protein level may be determined using Western blotting, ELISA (Enzyme-Linked ImmunoSorbent Assay), radioimmunoassay, immunohistochemical staining, immunoprecipitation assay and a protein chip.

The anticancer agent selected by the screening method of the present invention functions to induce premature senescence in tumor cells, thus exerting an anticancer effect.

WIG1 and YPEL5 genes, and proteins encoded by the genes, are found to account for premature senescence in tumor cells, as will be illustrated in the following Example section. Thus, a further aspect of the present invention envisages the use of an inhibitor against the gene or protein as an anticancer agent, and the use of a nucleic acid complementary to the mRNA or an antibody against the protein encoded by the gene in screening an anticancer agent.

Also contemplated in accordance with a still further aspect of the present invention is a method for treating cancer, comprising administering an inhibitor against a gene selected from the group consisting of WIG1, YPEL5, and a combination thereof, or against a protein encoded by the gene to an mammal including a human.

For use as an anticancer agent or in an anticancer composition or a method for treating cancer, the gene inhibitor, e.g., siRNA, and the protein inhibitor, e.g., an antibody, may be administered once a day at a dose of 0.01 ng/kg~100 mg/kg and at a dose of 2~10 mg/kg for adults, respectively. For administration, an intravenous route, an intra-arterial route, an intraperitoneal route, an intramuscular route, an intrathoracic route, a transdermal route, an intranasal route, an intrapulmonary route, a local route, an intrarectal route, an intraocular route, or a subcutaneous route may be used.

For use in the composition, method and use of the present invention, the nucleic acid, the antibody, the gene inhibitor or the protein inhibitor may be formulated together with a pharmaceutically acceptable vehicle. Examples of the pharmaceutically acceptable vehicle useful in the present invention include water, saline, phosphate buffered saline, dextrin, glycerol, ethanol, and a combination thereof. These components may be formulated into a rapid or sustained release dosage form. For formulation, reference may be made to Remington's Pharmaceutical Science (latest), Mack Publishing Company, Easton Pa.

For use in the present invention, WIG1 is encoded by a gene having the nucleotide sequence of SEQ ID NO: 1 {NCBI (National Center for Biotechnology Information) Access No. NM_152240} or SEQ ID NO: 2 (NCBI Access No. NM_022470), or by a mutant of the gene which results from the deletion, substitution or insertion of at least one nucleotide residue, and YPEL5 is encoded by a gene having the nucleotide sequence of SEQ ID NO: 3 (NCBI Access No. NM_016061), SEQ ID NO: 4 (NCBI Access No. NM_001127401), SEQ ID NO: 5 (NCBI Access No. NM_001127400), or SEQ ID NO: 6 (NCBI Access No. NM_001127399), or by a mutation of the gene which results from the deletion, substitution or insertion of at least one nucleotide residue.

It is obvious to those skilled in the art that the nucleotide sequences suggested for WIG1 and YPEL5 genes are only illustrative but are not limitative. It must be appreciated that a sequence having substantial sequence identity or similarity to those sequences falls within the scope of the present invention. As used herein, the term "substantial sequence identity" or "substantial sequence similarity" is intended to express a sequence which is substantially identical to a reference in terms of structure or function. The difference attributed to the mutation comes from, for example, a difference in codon usage between species. When there is a significant common or similar stretch on two or more different sequences, they are regarded substantially identical if showing similar physical properties although they are different in length or structure.

As to the genetic manipulation associated with the present invention, reference may be made to Sambrook, et al., Molecular Cloning, A Laboratory Manual, Cold Spring Harbor laboratory Press, Cold Spring Harbor, N. Y. (2001) and Frederick M. Ausubel et al., Current protocols in molecular biology volume 1, 2, 3, John Wiley & Sons, Inc. (1994).

Advantageous Effects

The method and composition according to the present invention make it possible to screen an anticancer agent, and the anticancer composition exhibit of the present invention exhibit anticancer effects.

MODE FOR INVENTION

Advantages and features of the present invention and methods of achieving them may be further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

Example 1

Screening for Anticancer Agent by Radiation-Induced Premature Senescence in Tumor Cell Line (1)

1-1. Cell Culture

The breast cancer cell line MCF-7 (ATCC, USA) was maintained in DMEM (Dulbeco's Modified Eagle's Medium) supplemented with 10% fetal bovine serum (FBS, Welgene), 100 µg/ml streptomycin and 100 units/ml penicillin (Gibco BRL) at 37° C. in a 5% CO2 humidified incubator.

After being exposed to a dose of 3.81 Gy/min of 6 Gy gamma-radiation from a 137Cs source gamma irradiator (Atomic Energy of Canada Ltd., Mississauga, Ontario, Canada), the breast cancer cell line was incubated for 1~4 days at 37° C. in a 5% CO2 humidified incubator.

For comparison, cells which were not exposed to gamma radiation were used as a control.

1-2. Radiation-Induced Premature Senescence

Figure 1:
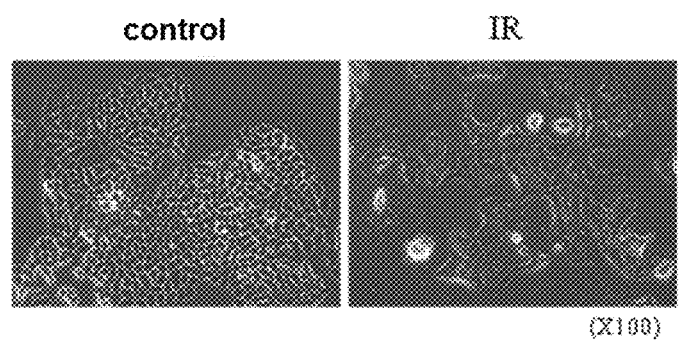
FIG. 1 shows phase-contrast microscopic images illustrating the senescence of MCF7 cell line at 4 days post-irradiation at a dose of 6 Gy (A), and a graph illustrating cell growth rates of the cell line (B).
Figure 1:
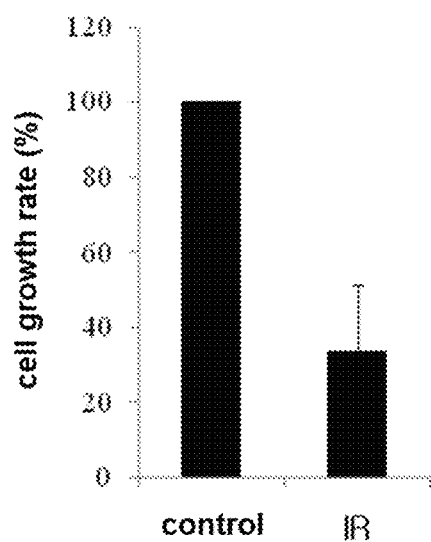

To examine whether the breast cancer cells were induced to undergo senescence, their morphological changes were observed under a microscope (ECLIPSE TE300, Nikon) four days after radiation exposure. The results are shown in FIG. 1A. Four days after radiation exposure, as can be seen in the microphotographs, the breast cancer cells became large in size and flat, which is characteristic of senescent cells, whereas the control remained morphologically unchanged.

In addition, an examination was made of cell proliferation. For this, cancer cells were seeded at a density of 1×10³ cells/dish onto 35 mm culture dishes and irradiated with radiation. Four days later, the cells were harvested with trypsin-EDTA (WelGENE Inc. Cat #LS 015-10) and stained with 0.4% Trypan blue (Gibco BRL, Cat #15250-061) to count live cells.

The radiation-exposed cells were found to significantly decrease in growth rate, compared to the control (FIG. 1B)

1-3. Identification of Radiation-Induced Senescence in Breast Cancer Cell Line by Senescence-Associated Beta-Galactosidase Staining To identify the induction of senescence in tumor cells by radiation, senescence-associated beta-galactosidase activity was detected in the breast cancer cell line four days after radiation exposure and in the control of Example 1-1 using a chromogenic substrate. This staining was performed according to the Dimri method (Dimri et al., Proc. Natl. Acad. Sci. USA, 92:9363-9367, 1995), as follows.

Cells were washed twice with PBS and fixed at room temperature for 3~5 min in 3% formaldehyde. The fixed cells were washed once again with PBS and incubated with 5 mL of a β-galactosidase staining solution (1 mg/ml X-Gal, 40 mM citric acid/sodium phosphate (pH 6.0), 5 mM potassium ferrocyanide, 5 mM potassium ferricyanide, 150 mM sodium chloride, 2 mM magnesium chloride) at 37° C. constant temperature incubator for 12~16 hours while the culture dishes were wrapped with foil so as to keep a dark condition.

Figure 2:
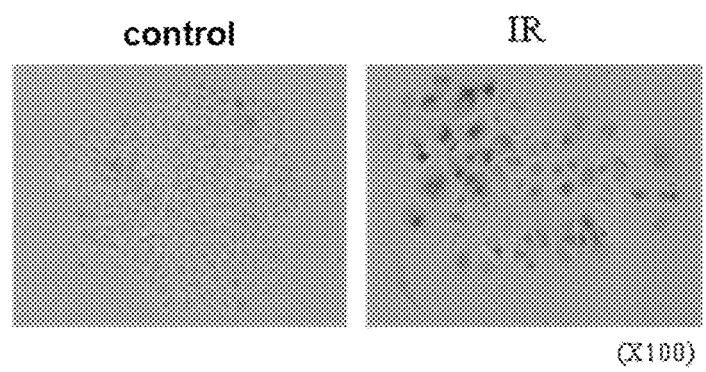
FIG. 2 shows images of MCF7 cells at 4 days post-irradiation at a dose of 6 Gy illustrating an increase in senescence-associated beta-galactosidase activity as visualized by staining (A), and a graph illustrating the proportion of beta-galactosidase-positive cells (B).
Figure 2:
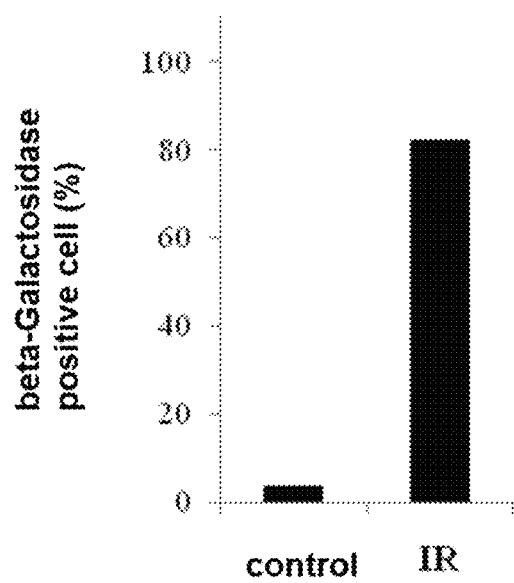

Beta-galactosidase activity was measured by phase-contrast microscopy (ECLIPSE TE300, Nikon), and the results are given in FIG. 2A.

In addition, most of the cells which remained alive at 4 days post-irradiation were found to show beta-galactosidase activity as a result of counting the number of the stained cells by using microscopy (ECLIPSE TE300, Nikon) (FIG. 2B), indicating that the cancer cell line clearly experienced senescence four days after irradiation.

Figure 3:
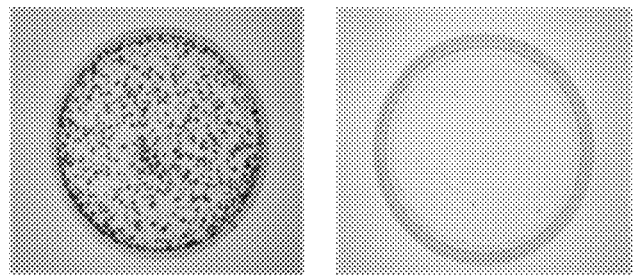
FIG. 3 shows images of tumor cell colonies formed 10 days after irradiation with a dose of 6 Gy (A) and a graph illustrating the count of the colonies (B).
Figure 3:
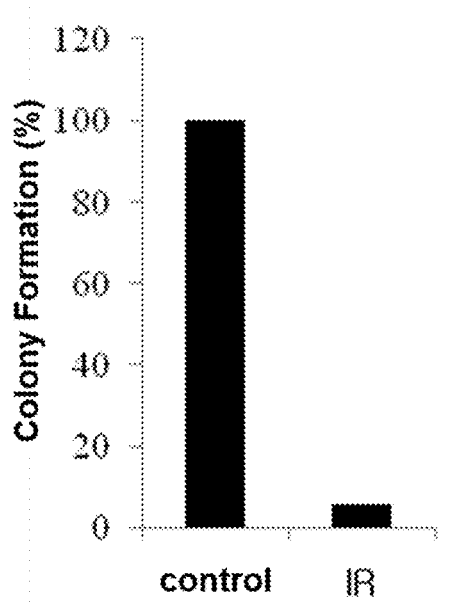

1-4. Identification of Radiation-Induced Senescence in Breast Cancer Cell Line by Colony Formation Assay The control and the radiation-exposed breast cancer cell line (MCF7) of Example 1-1 were distributed at a density of 500 cells/dish onto 60 mm dishes by passage. After incubation for 7~10 days, colonies thus formed were stained with a Diff Quick reagent (Sysmex Cat #38721). In detail, the medium was aspirated and the cells were washed once with PBS. Then, the cells were mixed softly with 0.5 mL of solution A and aspirated. The same procedure was repeated with solution B and solution C in that order. Thereafter, the cells were rinsed with a sufficient amount of distilled water and dried at room temperature for 30 min, followed by colony counting (Image Product International #880). No colonies were formed in the plates to which the radiation-exposed breast cancer cell line was applied (FIGS. 3A and 3B).

1-5. Microarray Assay for Identification of Gene Whose Expression Level Changes with Radiation-Induced Premature Senescence and Screening Anticancer Agent Using the Same At four days post-irradiation, the breast cancer cells (MCF7) prepared in Example 1-1 were rinsed with PBS and subjected to RNA isolation using TRI Reagent® (MRC, Inc. Cat #TR-118). The total RNA thus isolated was quantified using a UV spectrophotometer (Ultrospec 3100 PRO, Amersham Bioscience). cDNA was synthesized from 500 ng of the total RNA using reverse transcriptase, followed by in vitro amplification/transcription (Illumina® TotalPrep RNA Amplification kit, Ambion Inc.) to generate multiple copies of biotinylated cRNA from the cDNA template. 1.5 μg of the amplified biotinylated cRNA was hybridized to the BeadChip (Illumina Human-6 BeadChip®, Illumina, Inc.) and visualized with Cy3 fluorescence dye (Amersham Fluorolink streptavidin-Cy3, GE Healthcare Bio-Sciences). The chip was scanned on a confocal scanner (BeadStation 500GXDW; Illumina, Inc.) to detect hybridized signals which were analyzed using the software Illumina BeadStudio®.

This microarray assay identified genes whose mRNA levels were changed in the radiation-induced senescence cells relative to the control (Table 1).

Separately, the same procedures as in Examples 1-1 to 1-5 were repeated with the exception that the lung cancer cell line H460 (ATCC, USA) was used instead of the breast cancer cell line MCF-7, and the results are also summarized in Table 1 below.

TABLE 1

Genes Modulating in mRNA Level during Radiation-Induced Senescence in Tumor Cells

| | Cell Line | | | | |
|---|---|---|---|---|---|
| | MCF7 | | | | H460 |
| Expression Rate[1] | 1 D[2] | 2 D | 3 D | 4 D | 4 D |
| WIG1 | 2.0 | 3.3 | 3.2 | 3.7 | 6.9 |
| YPEL5 | 1.9 | 3.1 | 3.1 | 4.0 | 5.3 |

[1]rate relative to control (without irradiation)
[2]days after irradiation (6 Gy)

Therefore, the genes can be used to screen an anticancer agent which exerts anticancer activity on the basis of ability to induce senescence in tumor cells. To quote an example, an mRNA level of a gene selected from the group consisting of WIG1, YPEL5 and a combination thereof in a tumor cell line is measured by a DNA chip before and after treatment with an anticancer agent candidate (e.g., radiation, etc.). Selection is made of an anticancer agent candidate which causes the cells to increase the expression of the mRNA of the gene after treatment therewith. In detail, mRNA levels can be quantified with the WIG1 DNA probe (SEQ ID NO: 11) and/or the YPEL5 DNA probe (SEQ ID NO: 12) on the BeadChip.

In addition, it is understood that an inhibitor against the gene (radiation etc.) can exert an anticancer effect by cellular senescence in tumor cells.

Example 2

Screening for Anticancer Agent by Radiation-Induced Premature Senescence in Tumor Cell Line (2)

Figure 4:
FIG. 4 shows photographs of Western blots of WIG1 protein (A) and YPEL5 protein (B) illustrating an increase of protein expression level with time until four days after irradiation.
Figure 4:
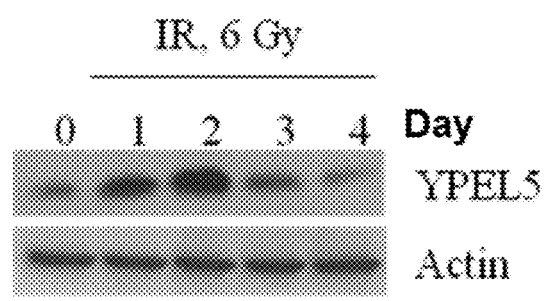

At 1~4 days post-irradiation, the breast cancer cell line (MCF7) prepared in the same manner as in Example 1-1 was rinsed in PBS (phosphate buffered saline) and lyzed with a cell lysis buffer (50 mM Tri-HCl, 1% NP-40, 0.25% sodium deoxycholate, 150 mM NaCl, 1 mM PMSF, 50 mM NaF, 0.2 mM Na3VO4, 10 g/ml aprotinin, 2 g/ml leupeptin), followed by centrifugation at 11,000 rpm for 10 min. The supernatant was taken to quantify proteins using the Bradford method {Bradford, M., Anal. Biochem. 72:248-254 (1976)}. 20 μg of protein was added to 2×SDS loading buffer (60 mm Tris-Cl (pH6.8), 25% glycerol, 2% SDS, 14.4 mM mercaptoethanol, 0.1% bromophenol blue), and the mixture was boiled at 95° C. for 5 min before electrophoresis at 80 V for 2 hours on 8% SDS polyacrylamide gel. The proteins separated on the gel by electrophoresis were transferred onto a nitrocellulose membrane (Whatman) which was then blocked in a 5% skim milk solution in PBS for 1 hour at room temperature. Thereafter, the membrane was incubated with a 1:500~1:1000 dilution of a primary antibody at 4° C. for 16 hours. The primary antibody was a polyclonal anti-WIG1 antibody (Santa Cruz) or anti-YPEL5 antibody (ProteinTech Group), while the secondary antibody was horse radish peroxidase-conjugated anti-rabbit antibody (Santa Cruz). Immunoreactive bands were read with an ECL (enhanced chemiluminescence) reagent (Amersham). Western blotting results are given for WIG1 in FIG. 4A and for YPEL5 in FIG. 4B. In the photographs, GAPDH or actin, a housekeeping gene which is expressed at constant levels in all cells, was used as a reference to show that the same quantity of proteins was employed for all experiments.

From one day after irradiation, expression levels of both WIG1 and YPEL5 proteins were increased, which was consistent with the results of the microarray assay of Example 1-5, indicating that mRNA levels of the genes were reflected in protein levels.

Therefore, the proteins can be used to screen an anticancer agent which exerts anticancer activity on the basis of ability to induce senescence in tumor cells. For example, a protein expression level of a gene selected from the group consisting of WIG1, YPEL5 and a combination thereof in a tumor cell line is measured with an antibody selected from the group consisting of an anti-WIG1 antibody, an anti-YPEL5-antibody and a combination thereof, before and after treatment with an anticancer agent candidate (e.g., radiation, etc.). Selection is made of an anticancer agent candidate which causes the cells to increase the expression level of the protein encoded by the gene after treatment therewith. In detail, the protein levels can be quantified with an anti-WIG1 antibody (Santa Cruz) or an anti-YPEL5 antibody (ProteinTech Group).

In addition, it is understood that an inhibitor against the proteins (antibody, etc.) can exert an anticancer effect by inducing cellular senescence in tumor cells.

Example 3

Identification of Anticancer Activity of WIG1 and YPEL5 Gene Inhibitors (siRNA) Based on Stress-Induced Premature Senescence in Tumor Cells 3-1. Injection of WIG1 and YPEL5 Small Interfering RNAs To examine the effect upon a reduction in the expression level of WIG1 and YPEL5 genes, the breast cancer cell line MCF-7 (ATCC, USA) was maintained in DMEM supplemented with 10% fetal bovine serum (FBS, Welgene) and an antibiotic (Gibco BRL) and passaged to 60 mm culture dishes one day before transfection with siRNA. In the OptiMEM®I medium (Invitrogen, Cat #31985), 3 µl of RNAiMAX (Invitrogen, Cat #13778-075) was diluted, and WIG1 or YPEL5 siRNA {siWIG1 (a duplex siRNA composed of nucleotide sequences of SEQ ID NOS: 7 and 8 with a two thymine (dTdT) 3' overhang on each strand) or siYPEL5 (a duplex siRNA composed of nucleotide sequences of SEQ ID NOS: 9 and 10 with a two thymine 3' overhand on each strand} was added. The resulting siRNA-reagent complex was added in an amount corresponding to an siRNA concentration of 50 nM to the cells, followed by incubation for 6 hours. After the medium was replaced by DMEM supplemented with 10% FBS (Welgene), 100 ug/ml streptomycin and 100 units/ml penicillin (both, Gibco BRL), the cells were incubated at 37° C. for 4 days in a 5% CO2, humidified incubator.

Separately, cells transfected with non-specific siRNA {having a core duplex composed of nucleotide sequences of SEQ ID NOS: 13 and 14 followed by a two thymine (dTdT) 3' overhang on each strand} were used as a control.

All of the siRNAs were synthesized in Bioneer (Korea). In detail, β-cyanoethyl phosphoramidite was employed for siRNA synthesis in such a manner that phosphodiester bonds were linked to construct the backbone of RNA (refer to Sinha et al., Nucleic Acids Research, 12:4539-4557, 1984). In an RNA synthesizer (Perseptive Biosystems 8909, PE Biosystems, USA), a series of processes including deblocking, coupling, oxidation and capping was repeated on nucleotides fixed to a solid support to a desired length of RNA. RNA was purified from the reaction mixture using HPLC LC918 (Japan Analytical Industry, Japan) equipped with Daisogel C18 (Daiso, Japan) and its sequence was analyzed by MALDI-TOF mass spectroscopy (Shimadzu, Japan). Then, sense and antisense RNA strands were combined to afford desired duplex siRNAs.

3-2. Determination of Decrease in Protein Expression by Specific siRNA

Figure 5:
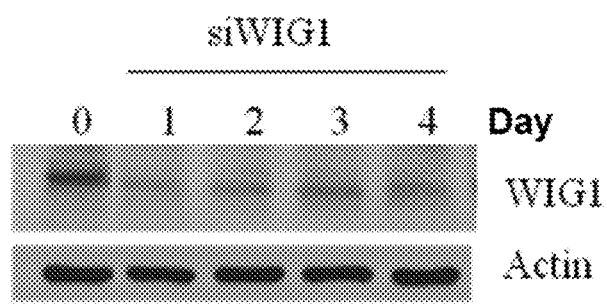
FIG. 5 shows photographs of Western blots of WIG1 protein (A) and YPEL5 protein (B) illustrating a decrease of protein expression level with time until four days after transfection with WIG1 siRNA (siWIG1) and YPEL5 siRNA (siYPEL5), respectively.
Figure 5:
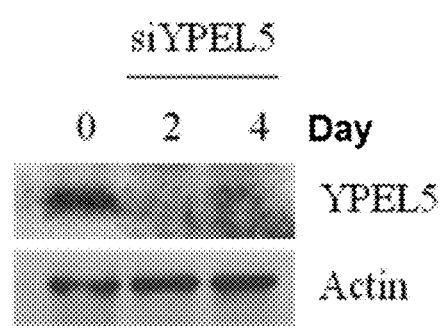

Reduction in the protein level of WIG1 or YPEL5 was identified in the same manner as in Example 2, with the exception that tumor cells transfected with siWIG1 or siYPEL5 were used instead of cells exposed to radiation. The results are shown in FIGS. 5A and 5B. FIG. 5 shows Western blots confirming the decrease of WIG1 and YPEL5 protein expression in the breast cancer cell line transfected with WIG1 siRNA (siWIG1) (A) and in the breast cancer cell line transfected with YPEL5 siRNA (siYPEL5) (B). In the Western blots, the housekeeping gene actin was used as a reference to show that the same quantity of proteins was employed for all experiments.

As can be seen, the expression levels of WIG1 and YPEL5 proteins were decreased below the control level until four days after transfection with siWIG1 and siYPEL5.

3-3. Identification of siWIG1 or siYPEL5-Induced Premature Senescence in Tumor Cell Line To examine whether the breast cancer cells of Example 3-2 became senescent, their morphologies were observed under a microscope (ECLIPSE TE300, Nikon) four days after transfection with siWIG1 and siYPEL5. Their images are given in FIGS. 6A (left panel) and 6B (left panel). FIG. 6A shows images of cells in which siWIG1 induced senescence at 4 days post-transfection (left panel), and FIG. 6B shows images of cells in which siYPEL5 induced senescence at 4 days post-transfection (left panel). Four days after transfection with siWIG1 or siPEL5, as can be seen in the images, the tumor cells became large and flat, which is characteristic of senescent cells, compared to the control.

Figure 6:
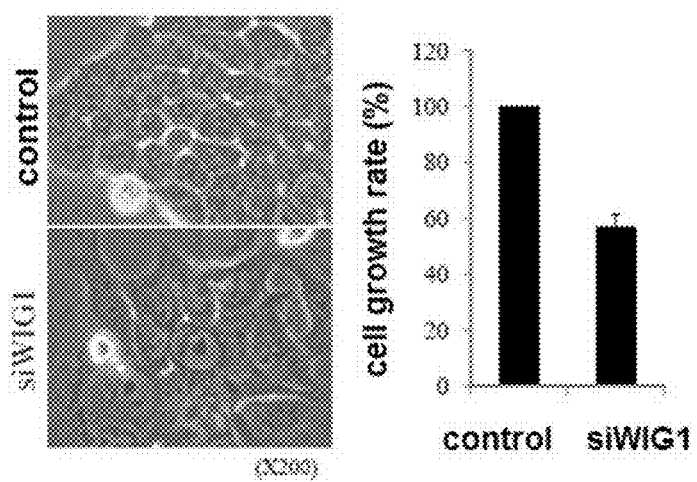
FIG. 6A shows images (left panels) of cells in which senescence has been induced until 4 days after transfection with siWIG1, and graphs (right panel) of cell growth rates in the cells.
FIG. 6B shows images (left panels) of cells in which senescence has been induced until 4 days after transfection with siYPEL5, and graphs (right panel) of cell growth rates in the cells
Figure 6:
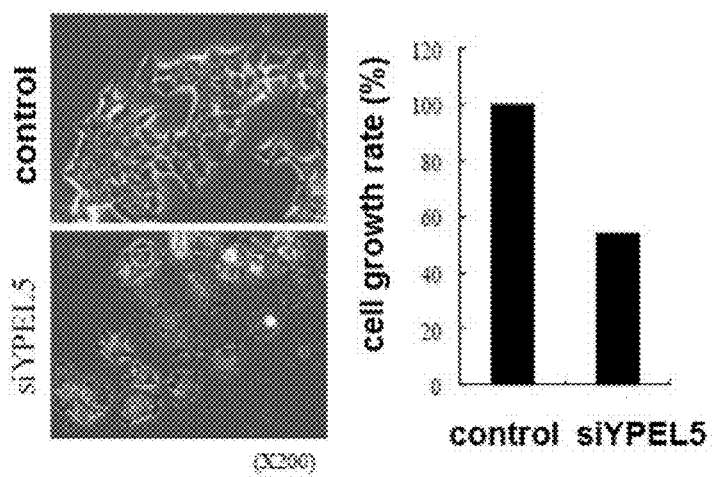

The same procedure as in Example 1-2 was repeated to measure cell growth rates, with the exception that the cells at 4 days after transfection with siWIG1 or siYPEL5 of Example 3-1 were used. The results are given in FIGS. 6A (right panel) and 6B (right panel). The right panel of FIG. 6A is a graph showing the growth rate of cells in which siWIG1 induced senescence at 4 days post-transfection, relative to that of the control. The right panel of FIG. 6B is a graph showing the growth rate of cells in which siYPEL5 induced senescence at 4 days post-infection, relative to that of the control. As can be seen in the graphs, the tumor cells were significantly reduced in growth rate by infection with siWIG1 or siYPEL5, compared to the control (FIG. 6).

3-4. Identification of siWIG1- and siYPEL5-Induced Senescence in Tumor Cell Line Using Senescence-Associated Beta-Galactosidase Staining The same procedure as in Example 1-3 was repeated with the exception that tumor cells at four days post-transfection with siWIG1 or siYPEL5 of Example 3-1 were used instead of the cells exposed to radiation.

Beta-galactosidase activity was observed by phase-contrast microscopy (ECLIPSE TE300, Nikon), and the results are shown in FIGS. 7A and 7B. FIG. 7A shows images (left panel) and a bar graph of proportions (right panel) of senescence-associated beta-galactosidase-positive cells at 4 days post-transfection with siWIG1, and FIG. 7B shows images (left panel) and a bar graph of proportions (right panel) of senescence-associated beta-galactosidase-positive cells at 4 days post-transfection with siYPEL5.

Figure 7:
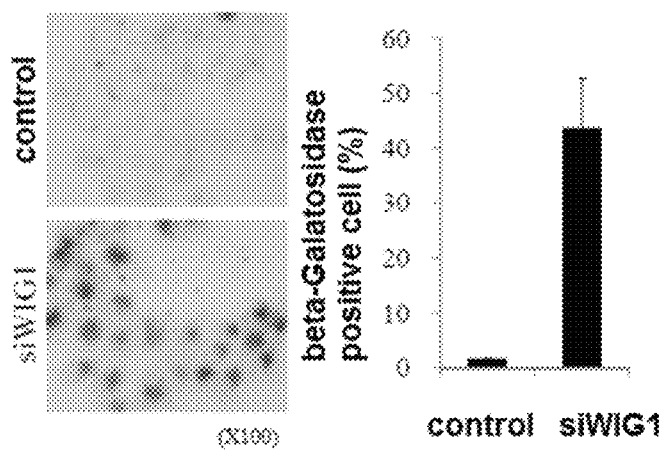
FIG. 7A shows images (left panels) of senescence-associated beta-galactosidase-positive cells at 4 days post-transfection with siWIG1, and graphs (right panel) of cell growth rates in the senescence-associated beta-galactosidase-positive cells.
FIG. 7B shows images (left panels) of senescence-associated beta-galactosidase-positive cells at 4 days post-transfection with siYPEL5, and graphs (right panel) of cell growth rates in the senescence-associated beta-galactosidase-positive cells.
Figure 7:
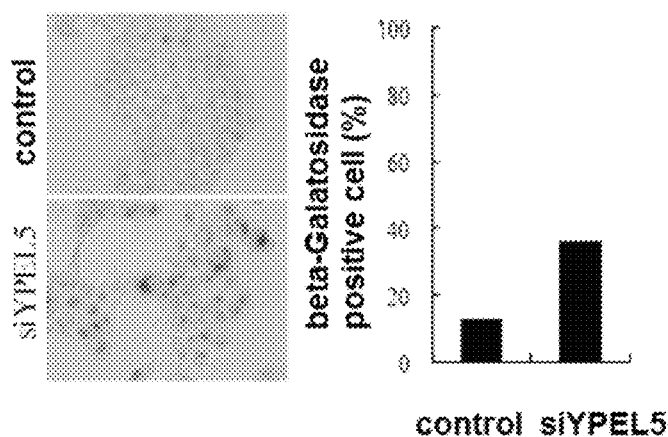

Compared to the control, a significantly greater count of the transfected cells was stained at 4 days post-transfection. Accordingly, beta-galactosidase activity was potentiated in the tumor cells four days after transfection with siWIG1 or siYPEL5, indicating the significant progression of senescence therein, whereas the control tumor cells experienced no senescence (FIG. 7).

Figure 8:
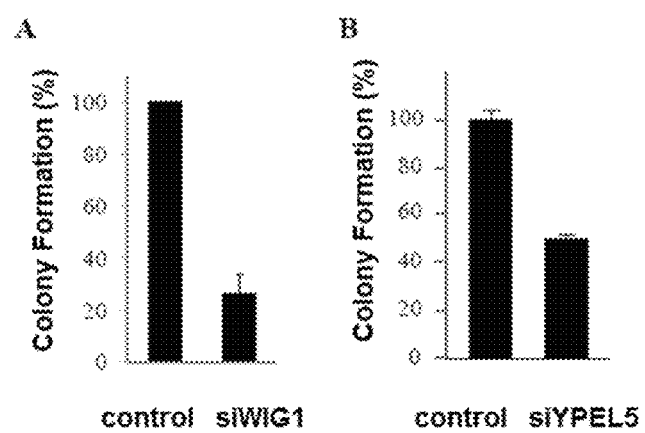
FIG. 8 shows graphs illustrating numbers of the colonies formed during 10 days after infection with siWIG1 (A) and siYPEL5 (B).

3-5. Identification of siWIG1- or siYPEL5-Induced Senescence in Tumor Cell Line by Colony Formation Assay The same procedure as in Example 1-4 was repeated with the exception that tumor cells transfected with siWIG1 or siYPEL5 of Example 3-1 were used instead of the radiation-exposed cells. The results are given in FIG. 8 shows graphs illustrating the counting results of the colonies formed during 10 days after infection with siWIG1 (A) and siYPEL5 (B). As can be seen in the graphs, a significantly lowered number of colonies was detected in tumor cell groups infected with siWIG1 or siYPEL5, compared to the control (FIGS. 8A and 8B).

Accordingly, suppression of WIG1 or YPEL5 gene expression induces senescence in tumor cells.

Taken together, the data obtained above demonstrates that inhibitors against WIG1 and/or YPEL5 gene (e.g., siRNA, etc.) can exert anticancer activity by inducing senescence in tumor cells.

INDUSTRIAL APPLICABILITY

The present invention is industrially applicable since the composition according to the present invention exhibits anticancer effects, as well as the composition and the method of the present invention allow to screen an anticancer agents.

What is claimed is:

1. A method for inducing premature senescence in tumor cells comprising administering to a mammal in need thereof an effective amount of an inhibitor against a gene selected from the group consisting of WIG1 (wild-type p53 induced gene-1), YPEL5 (yippee-like 5) and a combination thereof, or against a protein encoded by the gene.

2. The method of claim 1, wherein the inhibitor is an siRNA.

3. The method of claim 2, wherein the siRNA has the sense sequence of SEQ ID NO: 7 or 9.

4. The method of claim 1, wherein the inhibitor against a protein is an antibody.

* * * * *